United States Patent
Zubarev et al.

(10) Patent No.: US 10,401,337 B2
(45) Date of Patent: Sep. 3, 2019

(54) METHOD AND APPARATUS FOR IMPROVED QUANTITATION BY MASS SPECTROMETRY

(71) Applicant: Thermo Fisher Scientific (Bremen) GmbH, Bremen (DE)

(72) Inventors: Roman Zubarev, Stockholm (SE); Yaroslav Lyutvinskiy, Stockholm (SE)

(73) Assignee: Thermo Fisher Scientific (Bremen) GmbH, Bremen (DE)

(*) Notice: Subject to any disclaimer, the term of this patent is extended or adjusted under 35 U.S.C. 154(b) by 1033 days.

(21) Appl. No.: 14/390,391

(22) PCT Filed: Mar. 28, 2013

(86) PCT No.: PCT/EP2013/056808
§ 371 (c)(1),
(2) Date: Oct. 2, 2014

(87) PCT Pub. No.: WO2013/149963
PCT Pub. Date: Oct. 10, 2013

(65) Prior Publication Data
US 2015/0073727 A1    Mar. 12, 2015

(30) Foreign Application Priority Data
Apr. 2, 2012 (EP) .................... 12162811

(51) Int. Cl.
*G01N 33/48* (2006.01)
*G01N 30/86* (2006.01)
*H01J 49/00* (2006.01)

(52) U.S. Cl.
CPC ...... *G01N 30/8679* (2013.01); *H01J 49/0009* (2013.01); *H01J 49/0027* (2013.01); *H01J 49/0036* (2013.01)

(58) Field of Classification Search
None
See application file for complete search history.

(56) References Cited

U.S. PATENT DOCUMENTS

| 2003/0111596 A1 | 6/2003 | Becker et al. |
| 2008/0091359 A1 | 4/2008 | Oresic |

FOREIGN PATENT DOCUMENTS

CN    101571526 A    11/2009

OTHER PUBLICATIONS

Mueller, et al., "Superhirn—a novel tool for high resolution LC-MS based peptide/protein profiling," Proteomics 7(19), 2007, pp. 3470-3480.

(Continued)

*Primary Examiner* — Larry D Riggs, II
(74) *Attorney, Agent, or Firm* — David A. Schell

(57) ABSTRACT

A method of quantifying analytes from mass spectral data, comprising: obtaining a first set of mass spectral data from a first set of analytes eluted from a chromatography column; obtaining a second set of mass spectral data from a second set of analytes eluted from a chromatography column; determining apparent abundances of analytes in each data set; selecting a target analyte and determining localized neighboring analytes by their locality to the target analyte with respect to retention time; determining a locally corrected abundance of the target analyte based on differences between the first and second data sets in the apparent abundance of the localized neighboring analytes; and quantifying the target analyte based on its corrected abundance. A majority of the neighboring analytes are typically substantially unchanged in actual abundance between the first and second data sets and can be used for aligning the abundances between the data sets.

22 Claims, 15 Drawing Sheets

(56) References Cited

OTHER PUBLICATIONS

Sysi-Aho et al., "Normalization method for metabolomics data using optimal selection of multiple internal standards", BMC Bioinformatics, 2007, vol. 8, (1), p. 93.
Wiener et al.,"Differential Mass Spectrometry: A Label-Free LC-MS Method for Finding Significant Differences in Complex Peptide and Protein Mixtures", Analytical Chemistry, vol. 76, (20), 2004, pp. 6085-6096.

METHOD AND APPARATUS FOR IMPROVED QUANTITATION BY MASS SPECTROMETRY

FIELD OF THE INVENTION

This invention relates to mass spectrometry, particularly quantitative mass spectrometry. The method may be utilised for analysis of mass spectrometric data, for example obtained from liquid chromatography mass spectrometry (LC/MS).

BACKGROUND OF THE INVENTION

Mass spectrometry is increasingly used not only for identification of samples but also for determination of their absolute or relative quantities. The identification and quantitation of disease-related and/or treatment-related changes in the abundance of biological molecules, such as proteins, is an important area of research. Changes in the abundance of particular proteins or their modifications, for example, can make the difference between health and disease for an organism. Furthermore, the development of proteomics techniques that focus on the identification of protein differences can improve our understanding of disease and the effectiveness of therapeutic interventions. In this area, mass spectrometric based proteomics is now a widely used technology.

Typically, such quantification by mass spectrometry is done by calibration of the mass spectrometric peak of a sample with a peak of a reference (i.e. a sample of known quantity). When only relative quantification is required, this may be done by comparison of two sample peaks or comparison of a sample peak and a reference peak, which is typically isotopically labelled. In one such labelling experiment known as Stable Isotope Labeling by Amino acids in Cell culture (SILAC), two cell populations are fed with an amino acid that is isotopically labelled differently in each case so that proteins containing such peptide will be easily identified in the mass spectrum owing to the known mass difference in the isotopes. The proteins from both cell populations can be combined and analysed together by mass spectrometry and the ratio of their identified peak intensities reflects their abundance. Examples of methods utilising isotopic labelling are described, for example, in Horii, Y. et al, "Polychlorinated Dibenzo-p-dioxins, Dibenzofurans, Biphenyls, and Naphthalenes in Plasma of Workers Deployed at the World Trade Center after the Collapse", *Environmental Science & Technology, American Chemical Society,* 2010, 44, 5188-5194; Armenta, J. M. et al, "Differential Protein Expression Analysis Using Stable Isotope Labelling and PQD Linear Ion Trap MS Technology", *J. Am. Soc. Mass Spectrom.,* 2009, 20, 1287-1302; and Cantin, G. T. et al, "Combining Protein-Based IMAC, Peptide-Based IMAC, and MudPIT for Efficient Phosphoproteomic Analysis", *Journal of Proteome Research,* 2008, 7, 1346-1351.

For ease of quantification using labelling, the "MaxQuant" package by the Max Planck Institute (MPI) for Biochemistry, Germany is currently at the forefront of data handling, as described in Cox, J. & Mann, M., "MaxQuant enables high peptide identification rates, individualized ppb-range mass accuracies and proteome-wide protein quantification", *Nature Biotechnology* 26, 1367-1372 (2008); and Cox, J. & Mann, M., "Computational Principles of Determining and Improving Mass Precision and Accuracy for Proteome Measurements in an Orbitrap", *Journal of the American Society for Mass Spectrometry,* 2009, 20, 1477-148.

In US 2008/091359 and in Marko Sysi-Aho et al: "Normalization method for metabolomics data using optimal selection of multiple internal standards", BMC BIOINFORMATICS, Biomed Central, London, GB, vol. 8, no. 1, 15 Mar. 2007 (2007 Mar. 15), page 93, a quantitative method for metabolites is described in which multiple internal standards are intentionally spiked into the samples. The standards may have the same chemical structure as some analytes, but they are synthesized using isotopic labelling. Normalization values are calculated in the method based on the known and measured abundances of the limited number of intentionally spiked standards. The same set of standards are used for normalizing all metabolites and there is a clear distinction between the molecules used as standards and those that are analytes. It estimates the chemical similarity of standards to target analytes by measuring covariability of standards and analytes over a set of LC-MS runs and infers weights for internal standards from this covariability. Overall, the algorithm addresses the problem of instrument response undergoing changes over a set of LC-MS runs, i.e. from run to run, and does not consider changes which appear during a single LC-MS run.

The need for isotopic labelling in experiments, however, adds complexity and cost. Furthermore, in some experiments it is not viable to compare peak intensities with calibrants present within the dataset and therefore so-called label-free quantitation is necessary.

A label-free method is described in Wiener, M. et al, Differential Mass Spectrometry: A Label-Free LC-MS Method for Finding Significant Differences in Complex Peptide and Protein Mixtures *Analytical Chemistry,* 2004, 76, 6085-6096. In that method, an algorithm is used for finding differences in mass spectrometry data taken from two samples. The algorithm uses the mass-to charge ratio (m/z), the retention time and intensity to compare the data from the samples at every (m/z, time) combination. Statistically significant differences based on a t-test, which persist in time (i.e. over a sufficient time range), are used for quantitation.

Commercial software called SIEVE for label-free, semi-quantitative differential expression analysis of proteins, peptides and metabolites is available from Thermo Scientific, which reduces effects of chromatographic variability between samples.

In US 2003-111596 (Becker et al), a quantitative method utilises a normalization (scaling) of the data but the subject of scaling is the whole mass spectrum, i.e. all ion signals appearing in a single mass spectrum. Thus, Becker et al normalize their "peaks" regardless of their retention time, i.e. uniformly across the whole LC-MS experiment. Since Becker et al use the same normalization value for the whole LC-MS run, they compensate for the average difference in instrumental response between different LC/MS runs, but they are unable to compensate for such time-dependent sources of variability, as the fluctuations in the electrospray current, ionization efficiency and instrumental sensitivity that occur within the same LC-MS run.

A label-free approach, however, makes the quantitative data even more susceptible to variations. Such experiments are typically liquid chromatography mass spectrometry (LC/MS) experiments employing electrospray ionization (ESI). Aside from variations in sample preparation and chromatography, which can be minimized, a major contributor to the variation of peptide abundances in a label-free LC/MS experiment is the fluctuation of the ESI current. The fluctuations occur on all time scales, from milliseconds to minutes and hours. Although the total ESI current can be monitored by the instrument and recorded in the dataset, taking it into account presently leads to limited quality improvement or no improvement at all. This is probably because the main contributors to the ESI current are background ions whose composition is very sensitive to the LC gradient, ambient air or nebulizer gas quality and spraying conditions.

In view of the prior art described above, there is a need to improve the accuracy of quantification in LC/MS. It is desirable to bring the accuracy of label-free quantification closer or similar to that of labeling experiments (e.g. iTRAQ, TMT and SILAC). Against this background the present invention has been made.

SUMMARY OF THE INVENTION

According to an aspect of the present invention there is provided a method of quantifying one or more analytes from mass spectral data, comprising:

obtaining a first set of mass spectral data from a first set of analytes eluted from a chromatography column;

obtaining a second set of mass spectral data from a second set of analytes eluted from a chromatography column; wherein a majority of the analytes in each data set are common to both data sets;

determining apparent abundances of at least some analytes in each data set;

selecting an analyte as a target analyte and determining for that analyte a plurality of localised neighbouring analytes by their locality to the target analyte with respect to retention time; and determining a locally corrected abundance of the target analyte based on differences between the first and second data sets in the apparent abundance of the determined localised neighbouring analytes.

The invention further provides quantifying the target analyte based on its corrected abundance. Quantifying the target analyte may be quantifying either a relative quantity or an absolute quantity of the target analyte.

Preferably, the method further comprises selecting one or more further analytes as target analytes and for each such further analyte as a target analyte:

determining for that further analyte a plurality of localised neighbouring analytes by their locality to that further analyte with respect to retention time;

determining a locally corrected abundance of that further analyte based on differences between the first and second data sets in the apparent abundance of the determined localised neighbouring analytes; and optionally quantifying that further analyte based on its corrected abundance; wherein the plurality of determined localised neighbouring analytes is different for at least some different target analytes.

The method is preferably, though not of necessity, at least partly implemented in computer software. Mass spectral data may be obtained on a mass spectrometer and processing of the data may be implemented on a data processing system, such as a computer. The mass spectrometer may comprise the data processing system.

According to another aspect of the present invention there is provided a computer program having elements of program code for carrying out the method of the present invention, more specifically the data processing steps.

According to still another aspect of the present invention there is provided a computer readable medium carrying the computer program having elements of program code for carrying out the method of the present invention, more specifically the data processing steps.

According to yet another aspect of the present invention there is provided a mass spectrometer comprising a data processing system for carrying out the method of the present invention. The data processing system is preferably a computer that is programmed for carrying out the method of the present invention.

According to a further aspect of the present invention there is provided a mass spectrometer under the control of a controller, wherein the controller is configured such that the mass spectrometer is operable to perform the steps of the method according to the present invention. The controller is preferably programmed with the computer program according to the present invention.

The invention can significantly improve the processing of mass spectrometric data, especially chromatographic mass spectrometric data, to increase the accuracy of quantitation of analytes, especially biological molecules such as proteins, peptides, lipids and other entities.

The invention enables improved accuracy in label-free quantification by alignment of ion abundances, i.e. peak intensities, between complex mass spectral (especially LC/MS proteomics) data sets. This alignment reduces, for example, the effect of fluctuations of electrospray (ESI) current, which is a major source of error in label-free quantitative proteomics. It has been found that the accuracy of quantitation provided by the present invention in at least some cases can come close to that of SILAC experiments.

As a consequence of the improvement in data quality by performing the method of the invention, a smaller number of replicates may be used to achieve statistically significant results. Conversely, for a given number of replicated measurements, the statistics of the data are improved, thereby yielding greater reliability of results, for example in diagnostic applications.

The invention may be useful in LC/MS experiments employing fast and ultrafast chromatography.

Advantageously, the improvements provided by the invention are provided by data processing, without requiring changes in sample preparation, hardware, or workflow of LC/MS experiments.

The invention is preferably partially computer implemented, especially the data processing steps, and thus preferably comprises an automated data analysis method. The method is computationally efficient.

In contrast to the prior art, the invention not only accounts for chromatogram to chromatogram abundance variations (e.g. due to factors such as inexact dilution) but also makes a correction for the variability of instrument response within a chromatographic run (e.g. due to ESI current fluctuations), which can be significant.

In contrast to Wiener, M. et al cited above, the present invention implements a correction of a target analyte's abundance that is based upon an alignment of the abundances of neighbouring analytes in the close locality of the target analyte's retention time (i.e. retention time in the liquid chromatography column). In contrast to US 2008/091359, no standard is spiked into the sample, and therefore no concentration is known a priori. Instead of spiked standards, the neighbouring analytes are used as the "standards". That is, for a normalization step, the present invention makes use of the measured values of all available molecules that are naturally present in the sample (within a local retention time), without any other special limitations on the number or selection of such components.

The present invention differs from Becker et al where the same normalization value is calculated for the whole MS experiment, whether it is a LC-MS run or an individual MS spectrum. Instead, with the method of the present invention, a local normalization is employed that scales different parts of the same LC-MS run differently, as compared to the global normalization approach of the prior art (single normalization value used for the whole LC-MS experiment).

The invention makes use of the fact that a majority of the analytes in each data set are common to both data sets, i.e. are present in both data sets, and that it is typically the case that most of these common analytes have a substantially unchanged actual abundance (i.e. true abundance) between samples, e.g. in proteomics experiments. In a typical proteomics experiment, a significant fraction of all peptides have an actual abundance change less than the experimental uncertainty (>10%), i.e. are deemed substantially unchanged. Thus, the first set of analytes and second set of analytes are typically closely related in their identity with a majority of the analytes being substantially unchanged in their actual abundances between the first set and second set. These unchanged analytes (i.e. they have similar abundance in the two different samples) are used in the present invention for abundance alignment or fitting. In other words, unchanged analytes in the vicinity of a target analyte in retention time can be used as references to correct abundances, e.g. of the target analyte, between data sets at that retention time since fluctuations, for example of electrospray current and other factors, affect all simultaneously eluting analytes to the same degree. In complex mixtures, e.g. full-proteome digests, the analyte density is very high, e.g. thousands of peptides eluting over ca. 100 min of an LC gradient giving an average density >10 peptides per minute, thus there are enough analytes for representative statistics over the whole elution time.

Further details of the means by which the invention provides advantages are given below.

DETAILED DESCRIPTION OF THE INVENTION

The first set of analytes is typically from a first sample or first set of samples. The second set of analytes is typically from a second sample or second set of samples. The first and second samples or sets of samples may be a Case sample and Control sample respectively. The first set of analytes thus may be a Case set of analytes. The second set of analytes thus may be a Control set of analytes. In this way the absolute or relative quantities of one or more analytes may be compared between the Case set and Control set. The second or Control sample may be a reference sample containing one or more analytes of known abundance or concentration, thereby allowing the absolute abundance of the one or more analytes in the first or case sample to be determined. Alternatively, the second or Control sample may be of analytes of unknown abundance or concentration, thereby allowing only a relative abundance of analytes in the first or case sample to be determined (i.e. relative to the abundance in the second or Control sample). Often a relative abundance is all that is required, e.g. in differential expression experiments. The samples may be two different samples of a differential protein expression experiment for example. It will be appreciated that the invention can be applied to cases of more than two samples and thus, although for simplicity the invention is described herein primarily in relation to first and second samples or sets of samples (from which are respectively produced the first and second data sets), the scope of the invention, including as defined in the claims, is intended to include embodiments having at least two samples, i.e. not excluding embodiments having any further number of samples.

The first and/or second samples may each be samples made by pooling a plurality of other samples. Pooling in this way may, for example, reduce effects due to matrix variations across samples. Pooling of blood samples is one example.

The invention may be applied typically to the analysis of analytes in biological samples such as, for example, blood, urine, serum, cell lysate and others.

The first and second samples (Case and Control) are typically similar in the identity of the analytes that they contain and, in some embodiments may be near-identical (possibly even identical) with regard to the identity of the analytes that they contain.

In the invention, it is a feature that a majority of the analytes (i.e. greater than 50%) in each data set are common to both data sets, preferably at least 60%, at least 70%, at least 80%, or at least 90% (in order of increasing preference) of the analytes in each data set are common to both data sets. More preferably, more than 95% of the analytes in each data set are common to both data sets. In some cases, up to 98%, or in some case even more, of the analytes in each data set may be common to both data sets.

The invention makes use of this similarity in the compositions of the first and second sets of analyte by performing a local alignment of analyte abundances (i.e. mass spectral peak intensities) in the locality of each target analyte's retention time based on differences in the apparent abundances of analytes between data sets. A more accurate abundance correction can thereby be obtained for each target analyte than is possible using the prior art methods of label-free quantitative analysis. The local alignment of analyte abundances is able to account for ESI current fluctuations, which can occur on very short time scales and which cannot be adequately accounted for by mere scaling or normalisation of the total data sets to each other.

The samples may contain, for example, proteins, peptides, lipids, and other biological analytes, as well as non-biological analytes. The invention could be applied to the analysis of metabolites of a pharmaceutical in blood, urine, serum, cell lysate or other sample type. The analytes may thus be any of the aforementioned analytes, but are not limited thereto, i.e. proteins, peptides, lipids, pharmaceuticals and/or metabolites. In the case of proteins, the analytes eluted from the chromatography column and subject to the mass spectral analysis will be smaller peptides from a digestion of the proteins. However, from the quantitative analysis of the peptides by the method of the invention, the quantitation of the protein can be obtained. The invention is especially useful in proteomics where the analytes are peptides from the digest of a mixture of proteins.

Advantageously, the invention works on label-free analytes, i.e. non-isotopically labelled and non-chemically labelled analytes. However, it will be appreciated that the invention could also be applied to the measurement of labelled analytes.

The mass spectral data is preferably liquid chromatographic mass spectral data. The mass spectral data may be mass spectral data of the eluting analyte species (i.e. the parent analytes). Optionally, the mass spectral data may comprise MS/MS or $MS^n$ data, i.e. wherein the eluting analytes are selected by their mass-to-charge ratio (m/z)

after a first stage of MS and then fragmented so that their fragments are measured in a second stage of MS (i.e. MS/MS analysis). Yet further stages of MS may also be performed to obtain $MS^n$ data. Use of MS/MS or $MS^n$ measurements may be desirable when the identities of the analytes are not known beforehand so that it is necessary to identify the analytes using the mass spectral data. Thus, the step or steps of obtaining one or both of the data sets of mass spectral data may comprise obtaining a set of MS/MS or $MS^n$ mass spectral data from the set of analytes eluted from a chromatography column. Specifically, the method may comprise one of both data acquisition steps as follows: obtaining a first set of MS/MS or $MS^n$ mass spectral data from the first set of analytes eluted from a chromatography column; and obtaining a second set of MS/MS or $MS^n$ mass spectral data from the second set of analytes eluted from a chromatography column.

The MS/MS or $MS^n$ data may be used in a database search, or in de novo methods, to identify the analytes, as is known in the art. This approach may be applicable in the case of complex mixtures of analytes, such as peptides from a protein digest for example. Such analyte identification may be performed in post-processing or be performed on-the-fly, during data acquisition. However, in cases where the identities of the analytes are already known, e.g. prior to the LC/MS experiment, an MS/MS or $MS^n$ acquisition may not be required.

The first set of mass spectral data and/or the second set of mass spectral data may each independently be data obtained from a single chromatographic elution or from several chromatographic elutions (e.g. technical replicates or re-measurements). Each of the first set and/or second set could even be data from several chromatographic elutions which are from different (but closely related) samples (i.e. non-technical replicates).

The present invention is most preferably computer implemented. The invention comprises processing the obtained sets of mass spectral data, which processing is preferably performed using a computer (i.e. is computer implemented).

The processing of the sets of mass spectral data comprises: determining apparent abundances of at least some analytes in each data set; selecting an analyte as a target analyte and determining a plurality of localised neighbouring analytes to the target analyte with respect to retention time; and determining a locally corrected abundance of the target analyte based on differences between the first and second data sets in the apparent abundance of the neighbouring analytes. Further processing steps may be performed as described below, which are preferably computer implemented.

In embodiments, for example where the chemical identity of some or all the analytes in the data sets is not known or is not known fully or with sufficient confidence, the method may further comprise a step of identifying some or all of the analytes (e.g. peptides), preferably using MS/MS or $MS^n$ data, prior to the local abundance scaling step (see below) and preferably prior to the apparent abundance determination. The analytes may be identified using a database search, e.g. to match the obtained MS/MS (herein also including $MS^n$) peak patterns with those of known analytes or theoretical patterns contained in the database, or by de novo methods. The search may comprise comparing measured MS/MS fragment spectra with the theoretical fragments or stored library fragments of analytes assumed to be or possibly contained in the sample. The MS/MS measurements can therefore enable identification of an analyte from its fragment mass spectral data. As an example, if the sample is yeast, a database of yeast proteins may be "digested" to peptides using a computer algorithm, and these peptides "fragmented" using another algorithm, to give a number of predicted masses for each peptide and a number of predicted peptides for each protein. This is typically stored in a derived database which is typically indexed by peptide mass. The implementations of this may vary, e.g. the MS/MS simulation may be done on-the-fly. Thus, in the search the mass of a precursor ion can be used to identify a number of candidate peptides close to this mass and compare the MS/MS fragments calculated for this peptide to a measured MS/MS spectrum of the precursor ion to find the closest candidate match. Various programs exist for such MS/MS spectra interpretation, popular ones being Sequest and Mascot.

In other cases, some or all of the analytes may be known, i.e. pre-identified, such that their chemical identity is already known, and so they can also be termed identified analytes, even though a data processing step is not required or performed in order to identify them. Thus, herein the term identified analyte, means an analyte whose chemical identity is known, either before the experiment begins, or before data processing, or following an identification step, e.g. using MS/MS or $MS^n$ data as described.

In some cases, the MS/MS or $MS^n$ identification may be performed in a separate experiment, possibly on a related sample of higher availability (e.g. on a sample that is less precious, especially where the sample amounts are very limited).

The apparent abundances of the analytes may be, optionally, subject to a so-called global scaling or normalisation. This comprises adjusting the apparent abundances in one or both data sets so that the total analyte abundance is substantially the same for each data set.

The global scaling or normalisation may comprise a step of scaling the first set of mass spectral data and/or the second set of mass spectral data so that after scaling they have the same integrated total ion current (TIC) (global scaling). Preferably, this scaling of the first set of mass spectral data and/or the second set of mass spectral data comprises applying a common scaling to all the data in a set, so that after scaling the first and second sets have the same integrated total ion current (TIC). Thus, after this scaling, the total abundance of all the analytes (as determined from their ion peak intensities in the mass spectral data) in the first set of mass spectral data becomes the same as the total abundance of all the analytes in the second set of mass spectral data. For example, this so-called global scaling of the data can be performed such that the TICs of each data set after scaling give a common integral value, for example 1, or 100, or $1 \times 10^6$, or $1 \times 10^9$ arb. units (a.u.). The subsequent steps then use only the globally scaled data sets wherein the total analyte abundance has become substantially the same for each data set. The optional global scaling step (scaling the first and/or the second mass spectral data sets so that they have the same integrated total ion current (TIC)) may be performed after or before the optional step of identifying the analytes. Such a form of optional global scaling step, where used, is preferably performed prior to the local scaling or peak alignment steps, or apparent abundance determination, or even prior to the analyte identification step.

In another embodiment, the global scaling or normalisation may comprise adjusting the determined apparent abundances of the analytes, in one or both data sets, i.e. after the analyte abundances have been determined, so that the total (apparent) analyte abundance becomes the same for each data set.

The apparent abundance of identified analytes in each set of mass spectral data, which is the abundance as determined from the mass spectral data (prior to determining the corrected abundance in accordance with the invention), may be determined in various ways. In one preferred embodiment, in each data set for each identified analyte, all of the peaks in the MS data from ions of an identified analyte are grouped together and the area under the grouped together peaks is determined. It will be appreciated that the presence of different peaks from ions of the same analyte may be due to different charge states and different isotopes for example. The area so determined thus represents the abundance of the analyte in the respective data set. It will also be appreciated that in other embodiments, it is possible to use less than all of the peaks from ions of each analyte to represent the analyte abundance. For example, it may be possible to use a specified plurality of peaks of each analyte, or only the base peak or most intense peak of each analyte. Alternatively, quantitative information may be derived based on a fit to the isotopic distribution of the analyte (e.g. using either a general model distribution for the substance class (e.g. "averagine") or the theoretical isotope distribution of an identified analyte.

In an optional step the method may further comprise creating an extracted ion chromatogram (XIC) of the analytes, i.e. an XIC for each data set. This preferably involves grouping together a plurality, for example all, of the ions from a single analyte (i.e. the peaks of all such ions), performing this grouping for all identified analytes and plotting the grouped ions against retention time. This provides an XIC of the identified analytes, i.e. containing peaks for each analyte against retention time. Peaks in the mass spectral data (m/z peaks) due to different ions of the same analyte should have peaks in time at the same retention time as each other. By grouping together a plurality, e.g. all, of the ions for each single analyte the statistics can be improved. The different types of ions (peaks) for a single analyte preferably include all charge states and isotopes. However, as an alternative to grouping together all the ions from a single analyte, it is possible to perform the method using less than all the ions for each analyte. For example, only some ions (i.e. only some peaks) for each analyte may be grouped together, for example omitting one or more of the least intense ions. In some cases, it may be sufficient to use only a single ion, for example, the most intense ion or base peak. The XIC accordingly may be provided by plotting such representative ions representing each analyte against the retention time. Methods for chromatographic peak detection and forming the XIC are known in the art. A preferred such method that can be used with the present invention is described in EP 2322922. When using a method such as described in EP2322922 combined with a good chromatography (i.e. retention time) alignment method the identification step may be unnecessary. This is helpful in label free differential metabolomics or toxicology experiments, where the "matrix" is frequently not well understood.

Optional processing steps may be performed on the XIC including smoothing or peak fitting of the chromatographic peaks shapes to enhance the data quality.

The XIC can be used to determine, for each analyte peak, the peak area (or height) to represent apparent abundance as well as the retention time. Centroiding of the peak is preferably used to determine a retention time. Centroiding methods are well known. Other known methods of peak position determination could be used, for example peak fitting using a model peak or parabola.

When comparing two or more XIC, as hereinafter described, it may be found that the chromatograms differ significantly in shape. If so, they may still have a common part where the shape corresponds (for example, in a worst case, where only the three topmost points in time correspond). In such a case, for determination of a change of abundance between chromatograms, it may be preferred to use only that "common" or "consensus" part of the extracted ion chromatograms for computation of an abundance ratio.

The XIC is preferably performed prior to determining the n neighbouring analytes of each target analyte with respect to retention time. The n neighbouring analytes can thus be determined from the XIC. However, it is possible to get individual analyte abundance and retention time data of the n neighbouring peptides by directly mining the mass spectral data set without creating a separate XIC.

The identified analytes are aligned in both data sets, i.e. the peaks due to each identified analyte are located in each data set and associated with each other as belonging to the same analyte.

If any analyte has zero abundance in one data set it is preferably ignored in further processing. Occurrences of zero abundance may be detected, for example, by multiplying for each analyte the abundances of the analyte in the first and second data sets such that any zero value indicates that the analyte is not to be used for further processing (i.e. is not used in the correction of abundances). In other embodiments, it is possible to use an abundance of an analyte which has good signal-to-noise in one data set but zero abundance in another. Relative abundance of the analyte can be referred to the level of noise in the second data set in such cases.

If the first data set and the second data set each comprise data sets from several replicates, as is often the case, these replicate data sets should be aligned to each other. That is, the chromatographic peaks for each analyte should be aligned in the replicate data sets. Conveniently this is done by selecting one of the replicate data sets and aligning the other replicate data set(s) to the selected one. Alternatively, if a high number of replicate data sets is used for each of the first data set and the second data set, then it may be preferred to use for each an averaged data set which is an average of all the replicates. The (preferably retention-time aligned) replicate sets may be added together, e.g. to form either the first or second data sets.

A local abundance correction or scaling based on neighbouring analytes local to a target analyte is performed as now described in more detail.

In the step of selecting an analyte, i.e. an identified analyte, as a target analyte preferably this comprises selecting an analyte from the first set of mass spectral data. In the step of selecting an identified analyte, the identified analyte is an analyte that typically, although not necessarily, appears in both first and second data sets. The target analyte is typically an analyte which it is desired to quantify.

The localised neighbouring analytes are identified analytes common to both data sets that are close neighbours in retention time to the target analyte. Preferably as many analytes as possible within a suitable time interval spanning the retention time of the target analyte (local time interval) are used as neighbouring analytes, preferably including the target analyte itself as one of the neighbouring analytes for the abundance alignment. Preferably such local time interval for defining neighbouring analytes is at least as wide as the chromatographic peak width of the target analyte (measured at the peak base) and may typically be approximately the chromatographic peak width of the target analyte. The local time interval for defining neighbouring analytes may be less than twice the chromatographic peak width of the target analyte. Such local time interval is, for example, an interval of up to 0.5 minutes, or up to 1 minute or up to 2 minutes or up to 3 minutes, e.g. 0.5 to 2 minutes. However, the time interval may be longer than this if need be. The time interval spans the retention time of the target analyte. Preferably, the retention time of the target time is positioned at or near the middle (i.e. substantially at the middle) of the time interval used for defining neighbouring analytes. In this way, typically, neighbouring analytes will be selected from either side of the target analyte in retention time and the number of neighbouring analytes will be similar, or ideally equal, either side of the target analyte in retention time.

The number, n, of localised neighbouring analytes may be dependent on the number of species present in the sample. The number, n, of neighbouring analytes may range from just a few like 3, or 5, up to 7. The number, n, of neighbouring analytes may be for example, up to about 15 analytes, or up to about 25, or up to about 50, or up to about 100 analytes. The number, n, of neighbouring analytes thus may be in one of the ranges 3 to 100, or 3 to 50, or 3 to 25, or 3 to 15. The number, n, of neighbouring analytes may be in one of the particular ranges 3 to 15, or 15 to 25, or 25 to 50, or 50 to 100, or even more than 100. However, n<the total number of analytes and typically n<<the total number of analytes, i.e. n is much less than the total number of analytes, which could be hundreds or thousands such as in proteomics experiments. The group of n neighbouring analytes preferably includes the target analyte itself. Up to about 15 neighbouring analytes is statistically effective while being computationally efficient. Higher numbers of neighbouring analytes may not improve the statistics significantly further but all the time using higher numbers of analytes increases computational requirements. The number n is preferably at least 3, or 4 or 5, especially at least 5. Thus, an effective number n is typically from 5 to 25, more preferably 5 to 15, for example 6, 7, 8, 9 or 10. The neighbouring analytes should preferably be those n analytes that are located substantially the closest to the target analyte with respect to retention time, with the target analyte itself being preferably included in n. Typically, some analytes in the n neighbouring analytes will have longer retention times and some shorter retention times than the target analyte, i.e. the n neighbouring analytes typically will lie on either side of the target analyte with respect to retention time. The group of neighbouring analytes may span a retention time range of, for example, up to 0.5 minutes, or up to 1 minute or up to 2 minutes or up to 3 minutes seconds.

With regard to the neighbouring analytes, if any have a "suspicious" peak shape, such as a "tail" for example, this suspicious part may be removed from consideration, or the analyte may be discarded from consideration altogether as a neighbouring analyte, in the subsequent processing.

The step of determining a locally corrected abundance of the target analyte, may involve determining a corrected abundance of the target analyte in at least one of the first and second data sets. The corrected abundance may be a corrected absolute abundance or relative abundance, for example a corrected ratio of abundances between the first and second data sets. The process of determining a correction to the abundance of the target analyte based on differences in abundance of the neighbouring analytes between the first and second data sets preferably comprises determining a correction factor or factors based on differences in abundance between the first and second data sets of the neighbouring analytes and applying the correction factor or factors to the abundance of the target analyte to provide the corrected abundance.

The correction factor or factors, which are preferably a scaling factor or factors, preferably can be applied to the first or second set of mass spectral data, or both, to improve the correlation between the apparent abundances of the neighbouring analytes in the first and second data sets. That is, applying the correction factor or factors to the abundances of the neighbouring analytes improves the correlation between the apparent abundances of neighbouring analytes in the first and second data sets. The majority of the neighbouring analytes should be substantially unchanged in their actual abundance between the first and second data sets due to the nature of the experiment (e.g. in proteomics) so that an improved correlation represents an improvement in the quantitative value of the data. A linear correlation factor, for example, can be used to show an improved correlation between the abundances of the neighbouring analytes in the first and second data sets.

The abundance correction based on differences between the first and second data sets in the abundance of the neighbouring analytes is thus preferably based on those neighbouring analytes that are substantially unchanged in actual abundance between the first and second data sets. The majority of neighbouring analytes are preferably substantially unchanged in actual abundance between the first and second data sets. More preferably, at least 60%, or 70%, or 80%, or 90% (in order of increasing preference) of the neighbouring analytes are substantially unchanged in actual abundance between the first and second data sets.

It may be advantageous to remove any analytes from consideration as a neighbouring analyte when their abundance ratio between the data sets has already been determined from a previous calculation as being significantly changed. Conversely, already determined significantly changed neighbours, e.g. intense and high confidence neighbours, may be used for correction, but using their determined abundance ratio. The latter could be necessary if the number of "unchanged" neighbours becomes too small. If these type of "procedures" have to be employed it may be advisable to use at least a two-pass method for correction. In other words, a first-pass of the correction method is performed wherein all abundance ratios are determined (i.e. for all analytes identified in the data sets) and the corrections applied, followed by a second-pass of the method using "flags" from the first pass, wherein a flag may be, for example, an indication to remove an analyte from consideration or use a determined ratio or abundance for an analyte.

The correction factor or factors may be applied to the abundance of the target analyte in either the first data set or second data set or both. The process of determining a correction to the abundance of the target analyte based on differences in abundance between the first and second data sets of the neighbouring analytes preferably comprises steps of: determining from the neighbouring analytes a correction factor in the form of a value $K_{AV}$ representing a central tendency value of a ratio, K, wherein K is for each neighbouring analyte a ratio of its abundance in the first set of mass spectral data and its abundance in the second set of mass spectral data; and determining a corrected abundance of the target analyte based on the central tendency value, $K_{AV}$, of the abundance ratios K. The determination of $K_{AV}$ is described in more detail below. $K_{AV}$ may be a mean or median value of the ratios K, with or without weighting.

In such embodiments, once the neighbouring analytes have been determined, for each neighbouring analyte, the method preferably comprises calculating a ratio, K, of its abundance in the first set of mass spectral data and its abundance in the second set of mass spectral data. For calculating a ratio of abundances for each neighbouring analyte it is possible, for example, to use a ratio K of the abundance $A_1$ of the analyte in the first set of mass spectral data to its abundance $A_2$ in the second set of mass spectral data, i.e. $K=A_1/A_2$. In that case, to calculate a corrected abundance of the target analyte, the abundance of the target analyte in the first data set is divided by the average ratio, $K_{AV}$. Alternatively, to calculate a corrected abundance of the target analyte, the abundance of the target analyte in the second data set is multiplied by the average ratio, $K_{AV}$. For example, if the abundances of the neighbouring analytes are approximately twice as great in the first data set ($A_1$) compared to the second data set ($A_2$), such that $K_{AV}$~2, then the abundance of the target analyte in the first data set is divided by the $K_{AV}$ of ~2 to give the corrected target analyte abundance. Alternatively, the abundance in the second data set could be corrected by multiplying it by the $K_{AV}$ of ~2.

The ratio K may be a simple ratio of the abundances of an analyte in the different data sets, i.e. with no weighting (also referred to as a weighting of 1). However, on the assumption that more intense peaks (i.e. those with a good S/N) have lesser errors, preferably, each ratio K is given a weighting, such as is achieved, for example, by taking the ratio of the abundances described above and multiplying it by a weighting factor, or otherwise associating a weighting factor, W, with each ratio K. Such weighting factor should therefore preferably reduce the contribution of less intense peaks relative to more intense peaks. A suitable weighting factor may be the square root (sqrt) of the abundance (e.g. $A_2$) of the analyte in one of the data sets, e.g. the second (control) data set. Thus, the ratio K may be, for example, $K=(A_1/A_2) \cdot W$ where e.g. $W=sqrt(A_2)$. A square root weighting, for example, reflects the ion statistics effects in TOF instruments well, whereas for FTMS instruments a weighting with a sigmoid function may be preferred. Thus, a weighted mean $\overline{K}$ may be determined and used as $K_{AV}$. The weighted mean of is given by the following equation:

$$\overline{K} = \frac{\sum_{i=1}^{n} W_i K_i}{\sum_{i=1}^{n} W_i}$$

Where n is the number of neighbouring analytes as before and $W_i$ is the weighting for the $i^{th}$ analyte and $K_i$ is the ratio K for the $i^{th}$ analyte.

Better still than the mean, or a weighted mean, is to use the median or most preferably a weighted median for $K_{AV}$ as described in more detail below.

Herein, $K_{AV}$, refers to a value that represents the central tendency of the K values (abundance ratios) of the neighbouring analytes. The effects or influence of outlying K values on $K_{AV}$ are preferably reduced, more preferably excluded, when determining the average K value, $K_{AV}$. The invention thus preferably effectively determines an average $K_{AV}$ of so-called "unchanged" neighbouring analytes, i.e. neighbouring analytes which have not significantly changed in actual abundance between the data sets. For the unchanged analytes, the ratios K should thus be similar and may typically each be relatively close to unity, e.g. from 0.5 to 2.0. However, analytes which are "changed" in abundance will typically have K values significantly differing from most other analytes (assuming the typical case wherein most analytes are unchanged). These can be considered to be outliers in the set of K values. In other words, $K_{AV}$, is preferably an average value of the ratios K substantially from unchanged analytes. An average $K_{AV}$ that effectively ignores outlying values therefore should only reflect systematic variations in abundance between data sets.

The effects of outliers (outlying K values) can be effectively and conveniently reduced when determining $K_{AV}$ by selecting the median K value as $K_{AV}$. Since typically most K values, i.e. from the unchanged analytes, are similar and lie within a relatively narrow range, and only at most a small minority of K values are significantly outlying from this range, the median value will thus be a value from within the relatively narrow range and thus well representative of the K value of an unchanged analyte at approximately the same retention time as the target analyte (since it is determined from neighbouring analytes). The median is thus more preferred to the arithmetic mean (even a weighted arithmetic mean as described above). The arithmetic mean could be used but is less preferred since it does not exclude effects of outliers where it is the mean of all K values. Another preferred central tendency $K_{AV}$ would be the Winsorized mean.

A more preferred median to use as $K_{AV}$ is a weighted median, although an unweighted or conventional median can also be used with good effect. A method to determine a weighted median, comprises ordering the calculated ratios, K, in order of their size (i.e. either increasing or decreasing size). A weight W is calculated for each K (i.e. for each analyte). An example of a preferred weight for each K value has been found to be the square root of the abundance of the analyte in one of the data sets. With the ratios K for all the neighbouring analytes arranged in size order and each K having a weight associated with it, the weighted median value of K is given by the K value for which the sum of the weightings W for the K values below that K value is substantially equal to the sum of the weightings W for the K values above that K value.

Weighted medians may be calculated, for example, using the method described in A. I. Orlov: Econometrics course, publisher: "Examen" (in Russian) or as described at http:// www.stat.ucl.ac.be/ISdidactique/Rhelp/library/R.basic/ html/weighted.median.html (in English). The preferred weighting is the abundance square root, but a logarithmic weighting could be used. Weighting with sigmoids may also work well. Other methods of reducing effects of outliers in determining the $K_{AV}$ value could be to determine the average $K_{AV}$ using a majority but not all of the K values. In another method, of reducing effects of outliers for example only X % of the K values, wherein X is at most 80%, or at most 70%, or at most 60%, or at most 50%. Since the K values are mostly from unchanged analytes, restricting the number of the K values which are used to calculate the average $K_{AV}$ should reduce the likelihood of including a K value form an outlier in the calculation. More preferred would be to use the X % of K values which are the K values closest to the arithmetic mean of the K values or the K values in the middle of the distribution.

The value $K_{AV}$, being effectively determined from analytes which are nominally unchanged especially when a median is taken as $K_{AV}$, represents the degree to which the mass spectral peak intensities (and thus analyte abundances) have changed between the first and second data sets. Since the central tendency $K_{AV}$ is determined from unchanged analytes which are neighbouring in retention time to the target analyte, this provides a measure of the intensity and abundance change between data sets at that local retention time (and hence provides local scaling of abundance) and thus is a more accurate representation of the intensity or abundance fluctuation between data sets than achieved in the prior art. The value $K_{AV}$ can thus be used to correct the abundance of the target analyte in the first data set from which it was selected and the corrected abundance used for improved quantification of the target analyte.

Calculating a corrected abundance of the target analyte preferably comprises calculating a corrected abundance ratio, $K_{cor}$, of the target analyte in the first set of mass spectral data relative to its abundance in the second set of mass spectral data based on the ratio, $K_{AV}$. For example, $K_{cor}=(A_1/A_2)/K_{AV}$. It will be appreciated, however, that a corrected ratio may be expressed the other way around (i.e. where the ratio was expressed the other way around, $(A_2/A_1)$, namely as $K_{cor}=(A_2/A_1)/K_{AV}$. It may therefore be written as $K_{cor}=K_{targ}/K_{AV}$, where $K_{targ}$ is the ratio of the abundance of the target analyte in the first set of mass spectral data ($A_1$) relative to its abundance in the second set of mass spectral data ($A_2$), expressed either as $A_1/A_2$ or $A_2/A_1$. This provides a corrected relative abundance of the target analyte in the first and second samples (data sets). An absolute corrected abundance or quantity, $A_{cor}$ of the target analyte can be obtained from $A_{cor}=A_2 \cdot K_{cor}$. Thus, if the abundance $A_2$ is an absolute known value, e.g. if the second sample is a control sample having a known reference amount of the target analyte, then a corrected absolute amount of the target analyte $A_{cor}$ can be obtained.

The quantifying of the target analyte is thus either determining a relative quantity of the target analyte (e.g. the quantity of the target analyte in the first set of analytes (first sample) relative to the quantity of it in the second set of analytes (second sample), which may be expressed as a ratio K), or determining an absolute quantity of the target analyte based on the use of known absolute quantity of the target analyte in the second set of analytes (second or control sample).

Target analytes are selected from those analytes whose abundance has been determined. The method can be repeated for as many target analytes as desired. That is, the method typically will comprise repeating the steps of selecting a target analyte and determining a correction of its abundance for one or more further analytes. For example, a second target analyte can be selected and its n neighbouring analytes determined, followed by the remaining steps described above to arrive at a corrected abundance of the further target analyte. It is possible to vary the number of neighbouring analytes, n, for different target analytes but typically the same n will be used.

Target analytes can be selected based on pre-determined criteria, e.g. in proteomics experiments, target analytes may be peptides resulting from a digest of a protein the quantity of which is desired to be measured. Target analytes could also be selected based on the mass spectral data, for example by determining for all identified analytes the abundance ratios K and using threshold criteria selecting those analytes with sufficiently high K values as being candidate analytes whose abundance has significantly changed between the samples. Alternatively, in turn each analyte can be selected as a target analyte.

In cases where a plurality of replicate data sets (whether technical replicates or non-technical replicates) are produced, e.g. for each of the first data set and second data set, which is preferably the case to improve measurement reliability through improved statistics, each replicate data set may be used to determine a correction factor for correcting or aligning the target analyte abundances as described according to the present invention. For example, each of the replicates in one data set may be compared pair-wise to a plurality of replicates in the other data set and receive a plurality of pair-wise abundance alignments, i.e. correction factors, such as $K_{AV}$. For each target analyte the correction factor (e.g. $K_{AV}$) may thus be determined as an average (e.g. median) of the correction factors. This has the advantage that there is no unique "reference" data set but rather all data sets effectively become references. As a result, the statistics are more robust, and the outcome is more accurate.

Determining an expression factor or ratio (representing abundance difference between two samples) of an analyte in a plurality of samples such as replicate data sets can be done directly by making use of a "reference matrix". This comprises constructing a matrix of all the pair-wise ratios K (i.e. from all the different combinations of samples). The geometrical mean of each column of the matrix is calculated, which is given by the $n^{th}$ root of the column product. The geometrical means of the columns represent the expression factors of the analyte in the samples. An expression ratio between two samples is given by the ratio of the geometrical mean of the column representing one of the samples and the geometrical mean of the column representing the other of the samples. For example consider four samples. An example reference matrix may be constructed thus:

$$\begin{pmatrix} 1 & 1 & 2 & 2 \\ 1 & 1 & 2 & 2 \\ .5 & .5 & 1 & 1 \\ .5 & .5 & 1 & 1 \end{pmatrix}$$

The column 1 and 2 geometrical means (expression factors) are given by $$\sqrt[4]{1 \cdot 1 \cdot .5 \cdot .5} = \sqrt[2]{.5}$$

The column 3 and 4 geometrical means (expression factors) are given by:

$$\sqrt[4]{1 \cdot 1 \cdot 2 \cdot 2} = \sqrt[2]{2}$$

The expression factor ratio for sample 3 compared to sample 1 is given by the ratio of the respective column geometrical means$=\sqrt{2}/\sqrt{0.5}=2$.

From the determined quantity of the target analyte it may be possible to determine the quantity, relative or absolute, of a secondary analyte from which the target analyte is derived. For example, in proteomics a protein, typically a mixture of proteins, is digested and the resultant peptides are eluted in the LC/MS experiment. The peptides are thus the target analytes of the present method but the determined quantity of the peptide (analyte) is indicative of the quantity of the protein (secondary analyte) from which it is derived. Preferably, in such cases, all analytes (e.g. peptides) derived from a particular secondary analyte (e.g. protein) are grouped together and their corrected abundance compared in first and second data sets.

Use may be made of a reference matrix for determining protein expression factors. A matrix is constructed with elements: $a_{i,j}$ which are the ratio of protein abundances measured between samples i and j. The protein abundance is estimated as a median of abundances of peptides discovered in both samples for a particular protein. It is therefore proportional to the "true" abundance of the protein in the $i^{th}$ sample accurate within error $\delta_{i,j}$. The ratio of protein abundances may thus be taken as the median of its peptides abundances. The elements are inserted into a matrix like this:

$$\begin{bmatrix} a_{1,1}=1 & a_{2,1} & \ldots & a_{i,1} & \ldots & a_{n,1} \\ a_{1,2} & 1 & & \vdots & & a_{n,2} \\ \vdots & & 1 & a_{i,j} & & \\ a_{1,i} & \ldots & a_{j,i} & 1 & & \\ \vdots & & & & 1 & \\ a_{1,n} & a_{2,n} & \ldots & & & 1 \end{bmatrix}$$

A vector of protein expression factors may be formed from the columns:

$$\left[ \left( \prod_{i=1}^{n} a_{1,i} \right)^{1/n} ; \left( \prod_{i=1}^{n} a_{2,i} \right)^{1/n} \ldots \left( \prod_{i=1}^{n} a_{n,i} \right)^{1/n} \right] = [v_1; \ldots v_n]$$

An expression factor or ratio represents the variation in the abundance of an analyte. In another aspect, the invention further provides using the method of the present invention to identify analytes that are significantly changed in abundance between samples or groups of samples, i.e. between two samples or two groups of samples (wherein one sample or group of samples may be a control and another sample or group of samples the case). Identified analytes in this way be further reported by the method, for example as being analytes of potential further interest or significance. The analytes reported may be known (identified), or unknown (unidentified). A researcher could then make further use of the analytes, e.g. by seeing if they have a biological or medical significance. The samples analysed in this way could be blood (either human or non-human), as in the examples shown below, or any other biological samples, such as tissue (most likely dissolved in a known manner), urine, plant extract etc.

The invention thus provides a method in which the abundances of peptides are corrected according to the present invention and which comprises: determining variations in target analytes between two or more samples; and reporting analytes that show significant variations.

The significant variation may comprise a variation that is above a threshold, for example, outside a certain abundance ratio window. The significant variation may comprise variation that is significant based on one of the many statistical tests for defined certainty (e.g. above a certain probability threshold). Such tests may include the t-test, ANOVA etc.). The variation may include the appearance of the analyte in one sample or group of samples and its disappearance in another sample or group of samples. Typically, this is will require a good signal-to-noise ratio (S/N) in the sample or group of samples in which it appears, or appearance of the analyte in multiple technical replicates of one group and non-appearance in multiple technical replicates of another group.

In particular implementations, the method may further comprise determining a biological state from the determined analyte variations. For example, it may be known that one sample or group of samples is from healthy specimen(s) and the other sample or group of samples is from diseased specimen(s). In another case, it may be known that one sample or group of samples is from male specimen(s) and the other sample or group of samples is from female specimen(s). The determined analyte variations may thus be used to determine a biological state (e.g. healthy or diseased; male or female etc.) for a given sample. The method may also thus comprise assessing a state of disease in view of the determined variations. The method may also comprise finding a marker (such as an analyte that varies with disease state) for a disease.

It is preferable to perform one or more quality control measurements to ensure quality control of the method. For example, the average ratio $K_{AV}$ can be plotted across the retention time of the LC/MS experiment. The distribution should be relatively continuous with not more than minor sudden jumps in the $K_{AV}$ value. In another quality control measurement, between two technical replicates the ratios of the abundances of the analytes can be determined and the distribution of the abundance ratios can be plotted, which should be narrower after the data has been corrected using the method of the present invention. Similarly, a correlation plot between the abundances of the analytes for two technical replicates should show a greater correlation after abundance correction by the present method.

An additional possible method comprises performing a T-test for each protein. The T-test quality control method may also be applied to quantitatively assess variations of the method of the invention.

The method preferably comprises a step of outputting the result, e.g. the quantity of the analyte, and/or the quantity of a secondary analyte that is derived from the quantity of the analyte. Any of the data acquired, processed or generated, at any of the steps of the method, may be outputted if desired. Outputting means to a resource, i.e. tangible medium. Outputting may be to a resource such as a hard copy form, such as paper, or soft copy form as on a video display. Outputting may be to resource such as a computer readable data storage medium.

Any known suitable type of mass spectrometer can be used to obtain the mass spectral data, but preferably a mass spectrometer capable of high-resolution mass spectrometry and accurate mass measurement is used. With high resolution mass spectrometry, the exact masses of analytes can be used to align the analytes between the different data sets. Preferred examples include an orbital electrostatic trap (e.g. an Orbitrap™ mass spectrometer from Thermo Scientific), a time-of-flight (TOF) mass spectrometer, preferably a multiple-reflection TOF (MR-TOF), a Fourier transform mass spectrometer (FT-MS), for example an FT-ICR mass spectrometer, an ion trap, etc. The mass spectrometer may employ any suitable type of ion source, especially one compatible with liquid chromatography, such as, for example, electrospray ionization (ESI), including nanospray ionization, etc.

A chromatography device is interfaced to the mass spectrometer (e.g. LC/MS), i.e. such that at least some of the eluent from the chromatography device passes into the mass spectrometer for measurement of the mass spectral data.

The data processing steps performed on the data are preferably performed on a computer. The same computer may additionally control the mass spectrometer. The data processing steps may be implemented using a data handling package such as Microsoft Excel™ for example, or, more preferably, dedicated software that may also implement the whole method.

In a further aspect, the present invention provides a computer program having elements of program code which, when executed, carry out the method previously described. In still another aspect, the present invention provides a computer readable medium carrying said program.

The computer program preferably comprises elements of program code ("modules") that enable a computer system to implement a certain action associated with a module. Each step of the method may be implemented by one or more modules. The program preferably comprises a module for determining apparent abundances of at least some analytes in each data set; a module for selecting an analyte as a target analyte and determining a plurality of neighbouring analytes to the target analyte with respect to retention time; a module for determining a corrected abundance of the target analyte based on differences between the first and second data sets in the apparent abundance of the neighbouring analytes; and a module for quantifying the target analyte based on its corrected abundance.

The computer program and the computer readable medium preferably form part of a computer system, which is made operable by the program to perform the method of the invention and which includes at least one computer processor to execute the program code and perform the data processing. Processed data may be written to a storage system (e.g. computer memory). The computer system preferably comprises an input interface, e.g. to receive the data sets from the mass spectrometer. The computer system preferably comprises an output interface, e.g. to output the results. The computer system typically has a human user interface to enable a user to change or set certain parameters used by the method.

DESCRIPTION OF EMBOIDMENTS

In order to further understand the invention, embodiments will now be described in detail by way of example with reference to the accompanying drawings, which are for illustration only and are not intended to and do not limit the scope of the invention.

LIST OF FIGURES

Figure 1:
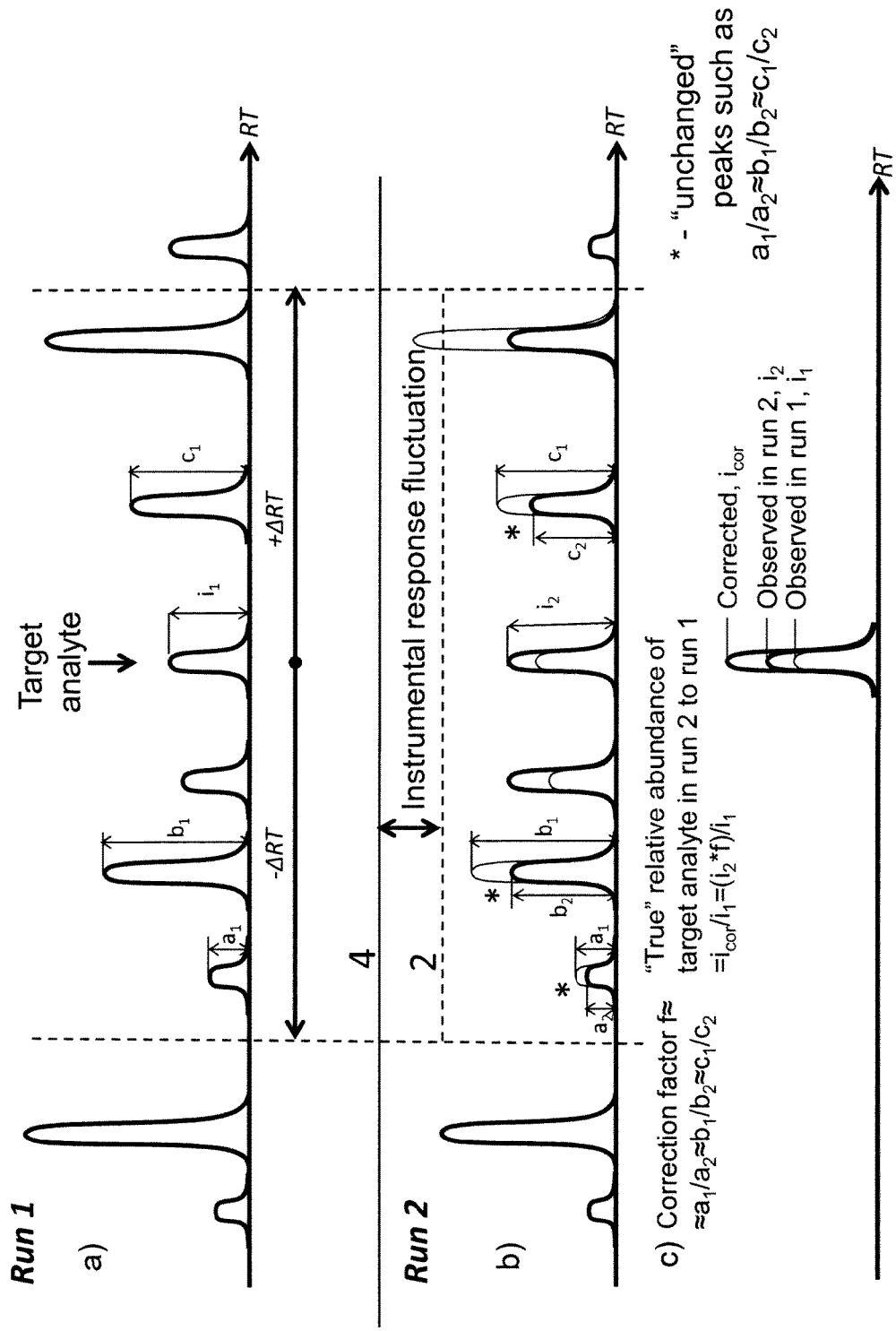
FIG. 1 shows schematically partial chromatograms for a Case chromatogram (a), a Control chromatogram (b) and a Corrected chromatogram (c) that has been corrected according to the present invention.

In one embodiment, two sets of LC/MS mass spectral data are obtained in a conventional manner from, respectively, a first sample, termed hereafter a Case sample, and second sample, hereafter termed a Control sample. The data sets are thus respectively termed hereafter a Case data set and a Control data set. Each of the Case data set and Control data set may comprise the data sets from two or more technical replicates. The samples are both digests of label-free protein samples which have by the nature of the experiment substantially the same qualitative protein content but different quantitative content for a small number of the proteins. Typically, less than 5%, or less than 2%, or less than 1%, or less than 0.1%, or even less than 0.01% of the proteins have a quantitative difference between the samples. In other words, the majority of the proteins are unchanged in quantity or abundance between the Case and Control samples, which reflects many real-life examples in the area of proteomics. The aim is to quantify the relative amounts of analytes, which in this example are peptides from the protein digest, present in the Case and Control samples. From the relative amounts of the peptides, the relative amounts of the proteins in the Case and Control samples can be derived.

It will be appreciated that the method is also applicable to other analytes than peptides. In other words, by substituting the peptides in the embodiments below with other suitable types of analytes the method can be applied mutatis mutandis.

Identification of Analytes and Alignment of Data Sets

Firstly, both sets of the mass spectral (MS) data are used for the purpose of identification of the peptides. Using both sets of data, rather than one, increases the reliability of the peptide identification. The mass spectral data includes MS/MS data and a database search using the MS/MS data is performed as known in the art in order to identify the peptides. The peaks in the MS data can then be assigned to particular peptides that have been identified.

Once the peptides have been identified, for each data set the peptide abundances are then determined. In this embodiment, in each data set for each identified peptide, all of the peaks in the MS data from ions of an identified peptide are grouped together and the area under the grouped together peaks is determined. For certain types of MS instrument, e.g. FTMS, abundance may be determined by the peak height. It will be appreciated that different peaks from ions of the same peptide may be due to different charge states and different isotopes. The area, or height, determined thus represents the abundance of the peptide in the respective data set. It will also be appreciated that in other embodiments, it is possible to use less than all of the peaks from ions of each peptide to represent the peptide abundance. For example, it may be possible to use only the base peak or most intense peak of each peptide, or a specified plurality of peaks of each peptide.

The peptide data for the Case and Control samples can then be aligned. For example a table can be compiled where the peptide identity is tabulated against its abundance in the Case and Control data sets, $A_{Case}$ and $A_{Control}$ respectively. The format of such a table may therefore look like table 1 below. The peptides can be sorted in any desired order, e.g. by sequence, modification, retention time etc. It is helpful for later processing to sort the peptides by retention time.

Optionally, this approach can be used to plot an extracted ion chromatogram (XIC) for each data set, in which the peptides are arranged by their retention time and the areas under the peptide peaks are determined from the XIC to provide the peptide abundance.

In one type of case, any peptides with zero abundance in any data set are removed from further processing. Such peptides may be identified and flagged for removal from further processing for example by creating a column in the aforementioned table 1 for the product $A_{Case} \cdot A_{Control}$, wherein any zero in that column acts as a flag to ignore that peptide.

In another type of case, any peptides with zero abundance in any data set are removed from further processing unless the peptide has an abundance with a good signal-to-noise ratio (S/N) in the other data set, in which case it is kept and the ratio K (see below) set to $A_{Case}/\text{Noise}_{Control}$. This is because sometimes a zero abundance may actually be important information.

Thus, peptides with zero abundance in any data set may be kept and the ratio K (see below) set to $A_{Case}/\text{Noise}_{Control}$ and/or flagged as missing etc.

TABLE 1

| Peptide Identity (ID) | Abundance, $A_{Case}$ | Abundance, $A_{Control}$ | $A_{Case} \cdot A_{Control}$ |
|---|---|---|---|
| Peptide #1 | | | |
| Peptide #2 | | | |
| Peptide #3 | | | |
| Etc. | | | |

Global Scaling of Abundances

The abundances of the peptides are optionally subject to a so-called global scaling or normalisation. This comprises adjusting the abundances in one or both data sets so that the total peptide abundance is the same for each data set.

This global scaling may optionally be carried out earlier, for example prior to abundance determination, by scaling one or both MS data sets so that the integrated total ion currents (TICs) of each data set become equal.

In the subsequent processing, these globally scaled abundances are used (where globally scaling is performed).

Abundance Ratios

The relative abundance ratio, K, of the Case and Control abundances, $(A_{Case}/A_{Control})$ for each peptide can then be calculated. Thus, a further column is preferably included in the table as shown in Table 2. Optionally, the ratio K is weighted, preferably by multiplying it by a weighting factor, such as the square root (sqrt) of $A_{Control}$ for example. A weighted K value is preferably used in the subsequent processing based on K.

TABLE 2

| Peptide Identity (ID) | $A_{Case}$ | $A_{Control}$ | Ratio, K $(A_{Case}/A_{Control})$ | Weighted Ratio, K $(A_{Case}/A_{Control}) \cdot$ sqrt $(A_{Control})$ |
|---|---|---|---|---|
| Peptide #1 | | | | |
| Peptide #2 | | | | |
| Peptide #3 | | | | |
| Etc. | | | | |

Local Scaling of Each Analyte Abundance

To provide an improved correction to the abundances, the invention provides a scaling of the abundance of each peptide of quantitative interest (target peptide) that takes into account local in time fluctuations in abundance.

For each target peptide, a group of neighbouring peptides in retention time is determined, typically those peptides with retention times in a specified local time interval spanning the retention time of the target peptide, especially spanning the peak width of the target peptide. The time interval is typically approximately the target peptide chromatographic peak width. This time interval may be up to about 2 minutes wide but in some cases may be only up to about 1 minute wide. The time interval is usually chosen such that the retention time of the target is at the centre of the interval. The group typically comprises at least 5 neighbouring peptides, and may comprise up to 100 peptides. More preferably, the target peptide is chosen at the centre of the group, i.e. with substantially equal numbers of neighbouring peptides on either side. Retention times of the peptides are obtained from the peptide peaks by centroiding for example, or other methods known in the art. If the Tables contain peptides aligned by retention time then the step becomes easier. By choosing neighboring peptides close in retention time, thereby ensuring that they are more or less simultaneously eluting with the target peptide, their abundance differences between data sets can be used to make an abundance correction that is localized to the target analyte.

It will be appreciated that the method can be performed whereby the described tables need only contain the target peptides and their determined neighbouring peptides. For example, only for these target peptides and their determined neighbouring peptides do their abundance ratios need to be calculated. In practice, however, it may be simplest to calculate the abundance ratio for all analytes.

The next part of the step involves using the neighbouring peptides that are unchanged in quantity or abundance (unchanged peptides) between the Case and Control, realizing that most peptides are in fact unchanged. The unchanged peptides, which are most of the peptides, typically will each exhibit a similar relative abundance ratio, K. Any changed peptides or spurious measurements will typically show up as outlying values of K. A reliable method of abundance correction has been found to result by taking a central tendency value, $K_{AV}$, of the ratios K substantially from the unchanged peptides. The value, $K_{AV}$ could be taken in several different ways. For example, $K_{AV}$ could be an arithmetic mean of the K values from the unchanged peptides (i.e. those with similar K values to each other) and ignoring the peptides with outlying K values. A particularly preferred and convenient method is to use a median value of the ratios K as $K_{AV}$, which ensures that the median is close to being the mean of the unchanged peptides without needing to identify outliers as such and that the effects of any outliers are effectively excluded from influencing the value of $K_{AV}$.

Correcting the Case/Control Ratio

After determination of $K_{AV}$, the Case/Control abundance ratio can be corrected accordingly to $K_{cor}=(A_{Case}/A_{Control})/K_{AV}$, where $K_{cor}$ is the corrected Case/Control abundance ratio.

A corrected abundance, $A_{Case\ cor}$ of the target peptide in the Case sample can be obtained from $A_{Case\ cor} = A_{Control} \cdot K_{cor} = A_{Case}/K_{AV}$. If the abundance $A_{Control}$ is an absolute known value then a corrected absolute amount of the target analyte can be obtained.

The quantification of the target peptide is used to quantify the protein from which is derived, typically together with quantification of other target peptides derived from that protein.

The method can be repeated for other target peptides, as many as desired.

Already corrected abundances of target peptides may be used in subsequent calculations of abundance corrections for target peptides.

The principle of operation of the method is illustrated schematically in FIG. 1. In FIG. 1(a) is schematically shown a part of a chromatogram (XIC) for a Case data set (Run 1) and in FIG. 1(b) the corresponding part of a chromatogram for a Control data set (Run 2). The peptide peaks are neighbouring peaks in retention time that have been aligned between the Case and Control. In FIG. 1(b) the average level of ESI current (instrument response) at approximately that retention time is shown, wherein the average instrument response (dotted line 2) was about 20% lower for the Control chromatogram than for the Case (solid line 4). For this schematic example, other factors leading to signal variations between Case and Control are not described but an advantage of the method of the present invention is that all sources of signal variations become accounted and corrected for. In FIG. 1(a) the Case abundances for several peptide peaks are shown: $a_1$, $b_1$ and $c_1$. In FIG. 1(b), the Case abundances (i.e. from chromatogram (a)) are shown for comparison with the corresponding Control abundances: $a_2$, $b_2$ and $c_2$. A target analyte i is shown which has an observed Case abundance $i_1$ in Run 1 and has an observed Control abundance $i_2$ in Run 2. As the peptide identity and abundances are mostly the same in the Case and the Control, a majority of the peaks in the chromatograms should be unchanged but for the 20% lower instrument response. In the schematic FIG. 1 chromatograms, within a given retention time window +/−ΔRT of the target analyte, the localized neighbouring peaks a, b and c are unchanged (i.e. minimal abundance change). In practice, in proteomics, the vast majority of peaks will be unchanged. Using only the unchanged peaks, the ratio $K_{AV}$ of the peak abundances between Case and Control ($A_{Case}/A_{Control}$) is obtained, which in this case is approximately 1.0/0.8 or 1.25. This provides a correction factor f from the neighbouring peaks≈$a_1/a_2$≈$b_1/b_2$≈$c_1/c_2$. In FIG. 1(c) is shown the corrected chromatogram (continuous line) $i_{cor}$ for the target analyte peak i wherein the Control peak has been corrected by scaling or normalizing the abundance by adjusting it by the amount required to produce a fit of the abundances of the unchanged peaks in the Case and Control, i.e. using the average abundance ratio $K_{AV}$ (correction factor f). Thus, the "true" relative abundance of the target analyte in Run 2 to Run 1=$i_{cor}/i_1$=$(i_2*f)/i_1$. The corrected abundance of the target peptide based on this localized abundance normalization can be used to determined a more accurate abundance change relative to the Control chromatogram.

Quality Control

Figure 2:
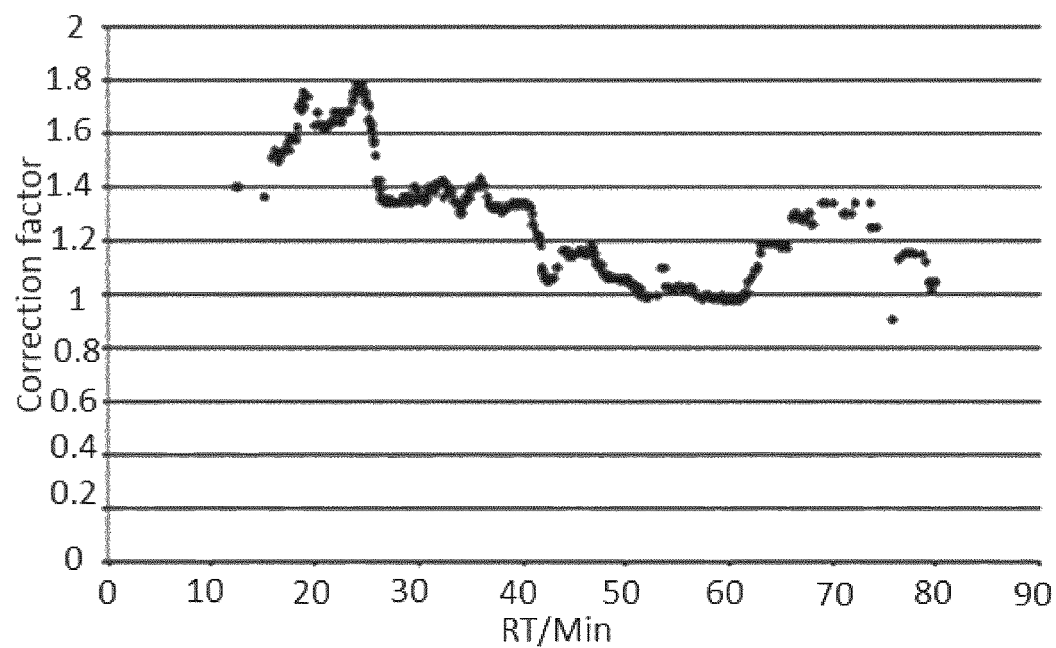
FIG. 2 shows a distribution of the correction coefficient across an LC/MS run for two technical replicates.
Figure 3:
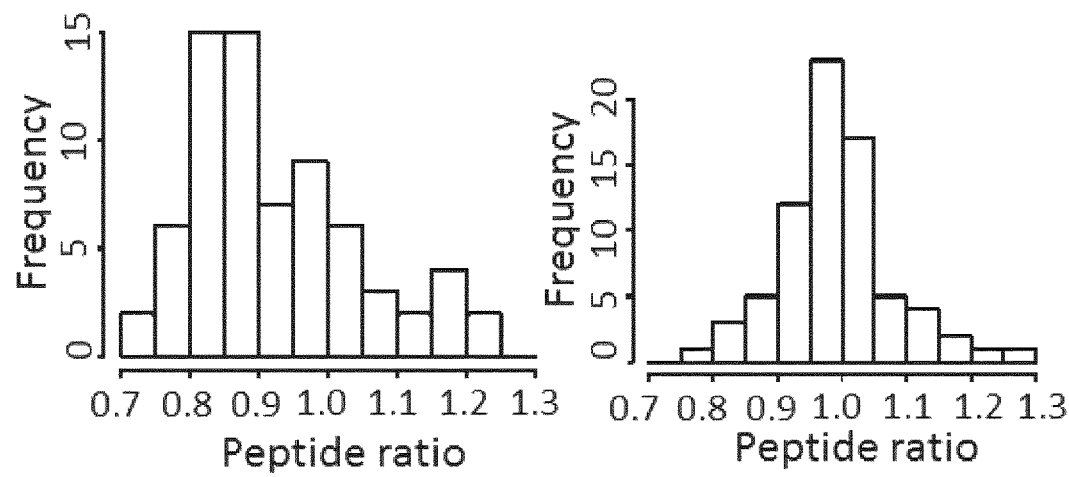
FIG. 3 shows a distribution of peptide abundances ratios before and after correction.
Figure 4:
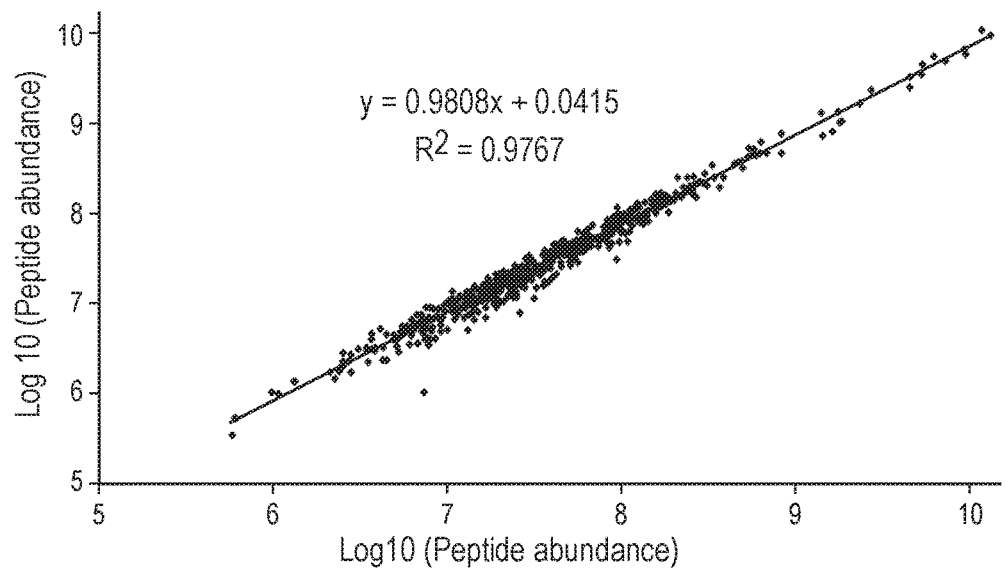
FIG. 4 shows a Correlation plot between two technical replicates without correction.
Figure 5:
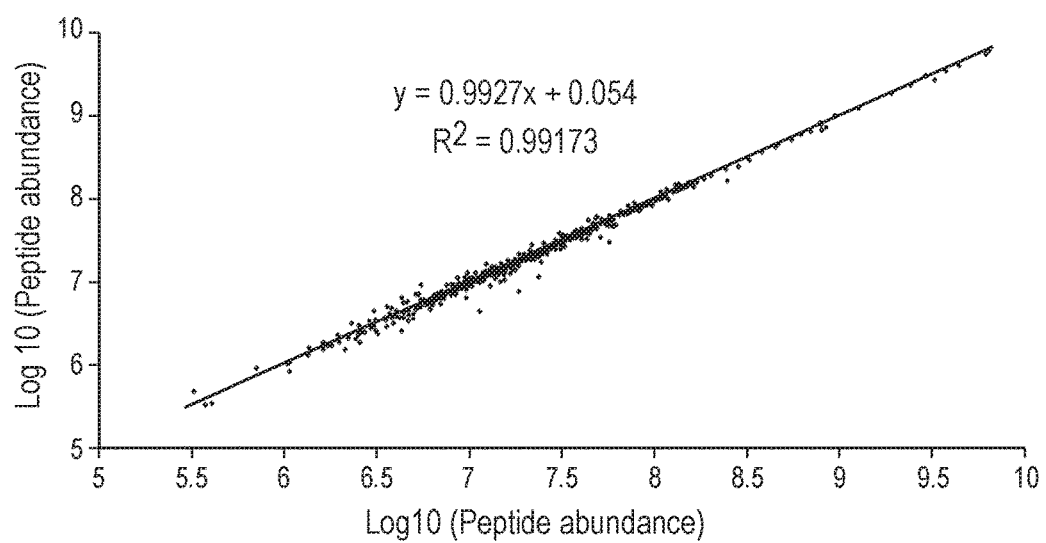
FIG. 5 shows a Correlation plot between two technical replicates after correction according to the present invention.

It is preferable to include in the method a check that the method is improving the alignment of abundances, i.e. quality control. There are several ways of performing quality control:

1) by monitoring the distribution of the correction factor, such as $K_{AV}$, across the LC/MS run (Retention Time, RT). The distribution should be a continuous line with only minor sudden "jumps" as shown in FIG. 2); and/or
2) by comparing two technical replicates of the same sample, the distribution of ratios of peptide abundances should become more narrow after correction of abundances (as shown in FIG. 3 where the left hand distribution (y axis=frequency; x-axis=peptide ratio) is before correction and the right hand distribution is after correction); and/or
3) by calculating the linear correlation factor $R^2$ between Case and Control abundances. This correlation factor should increase upon the abundance alignment. An example of the increased correlation between two technical replicates is shown in FIGS. 4 and 5. FIG. 4 is a correlation plot of peptide abundances before application of the correction method of the invention (x axis, sample 1, y axis sample 2) and FIG. 5 is a correlation plot for the same samples after application of the method of the invention. The two samples are technical replicates, i.e. they are fractions of the same sample, and thus the expected correlation $R^2$ for a perfect experiment is as close to 1.0 as possible.
4) by a T-test quality control method to quantitatively assess the abundance alignment of the method of the invention.

EXAMPLES

The examples below use blood plasma samples but it will be appreciated that the samples could be any biological samples.

Blood Plasma

An Orbitrap™ Velos MS system from Thermo Scientific was used to acquire LC/MS data from 8 blood plasma samples (label-free). The system was set-up with Proxeon™ nano-LC operated with a 120 min. gradient. Each of the 8 samples was pooled from 25 individuals. Each sample was then digested 3 times and then each digest run twice (i.e. 2 technical replicates) in the LC/MS system. Therefore, each of the 8 samples was run 6 times.

The acquired mass spectral data was then evaluated without the method of the invention (such results termed "before correction") and with the method of the invention (such results termed "after correction"). The data acquisition and processing is described in detail below.

FIGS. 4 and 5 show the correlation between two technical replicates before correction and after correction respectively. The data for the two technical replicates after correction clearly shows a much higher correlation. In fact, the after correction data has been found to be as good, or almost as good, as data from SILAC experiments.

Figure 6:
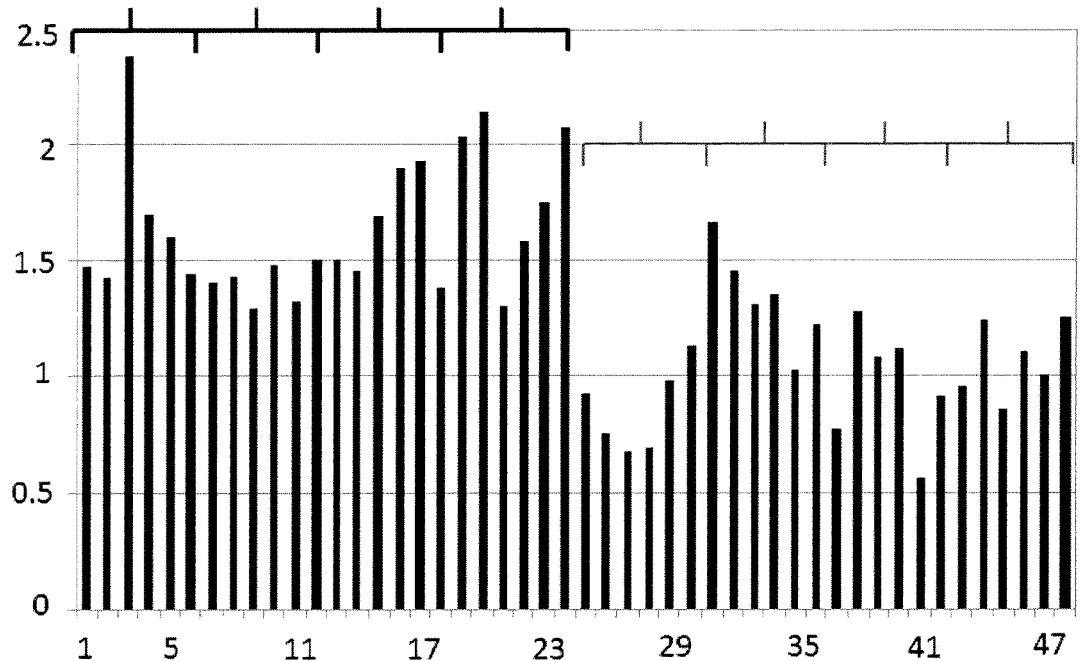
FIG. 6 shows the relative content between male and female blood samples of haptoglobin-related protein (HPR) for data before correction, which can be used for assessing a biological state.
Figure 7:
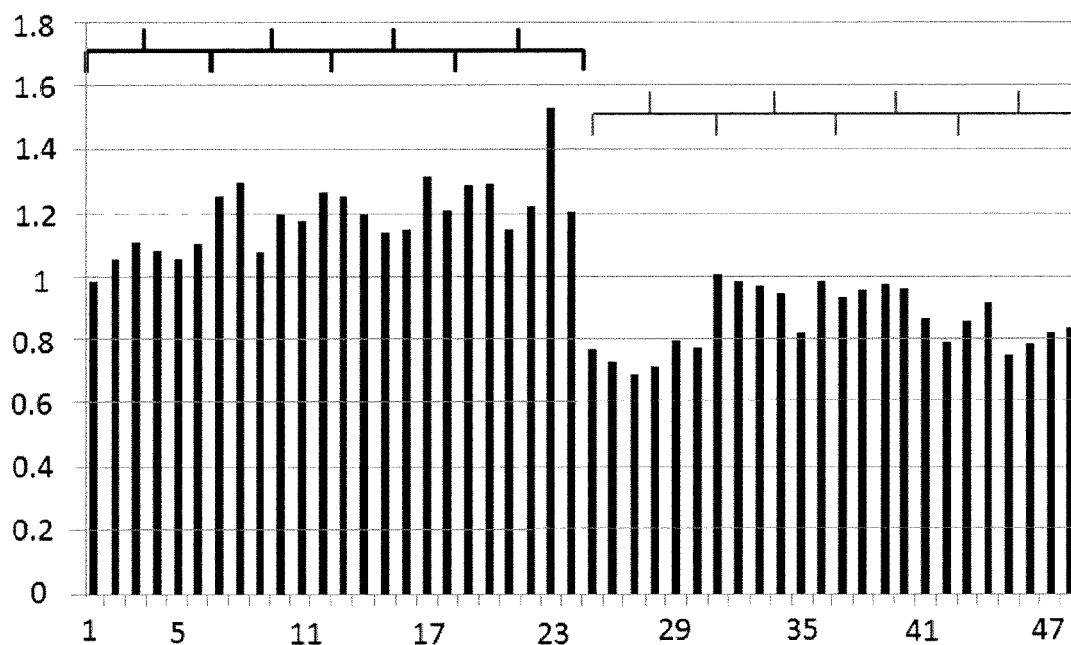
FIG. 7 shows the effect on the data in FIG. 6 of an abundance correction according to the present invention.
Figure 8A:
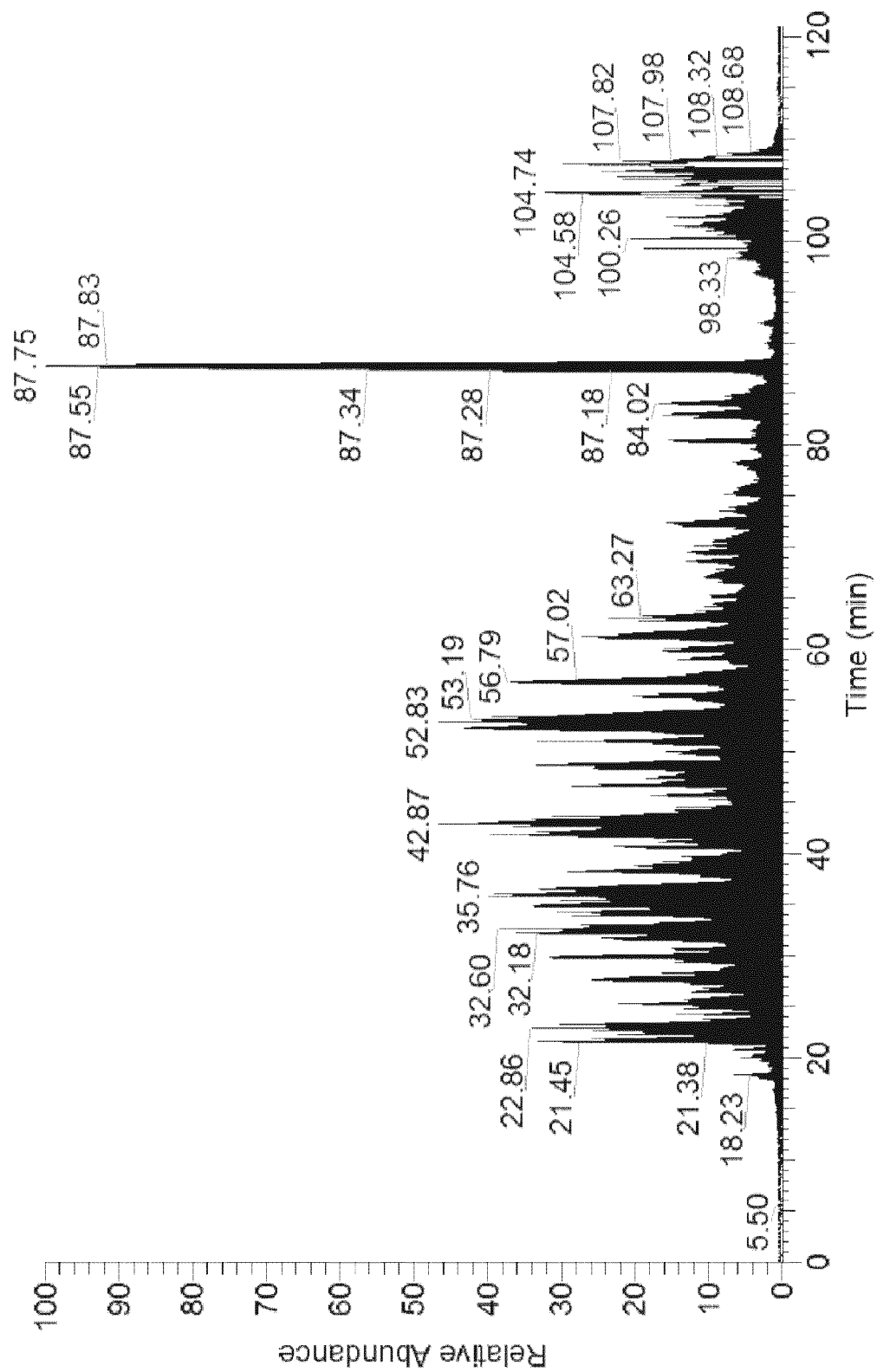
FIG. 8 shows the total ion current (TIC) chromatograms analysed with Orbitrap MS for two technical replicates of each of CM (left hand) and M1 (right hand) groups.
Figure 8B:
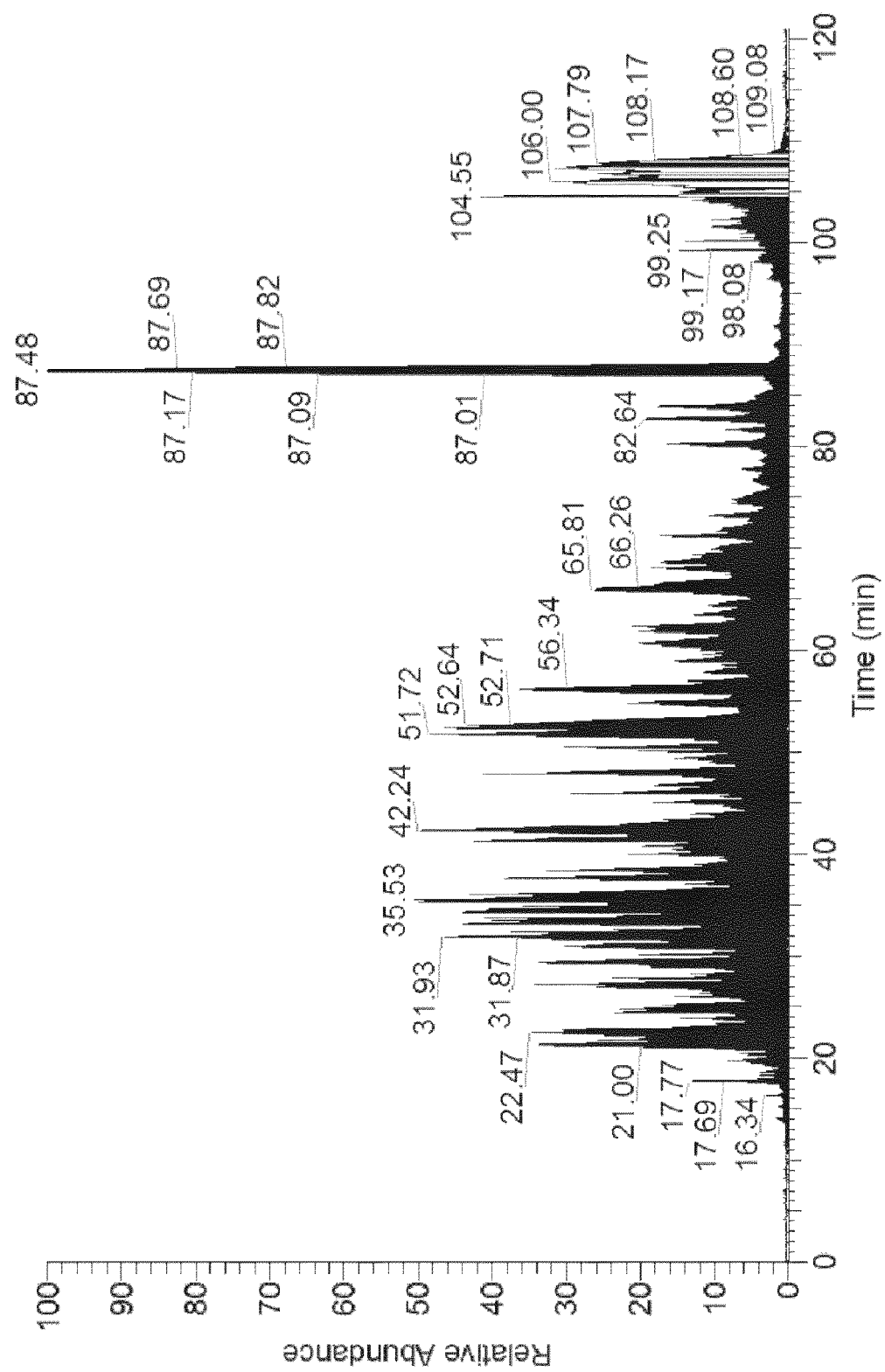
Figure 8C:
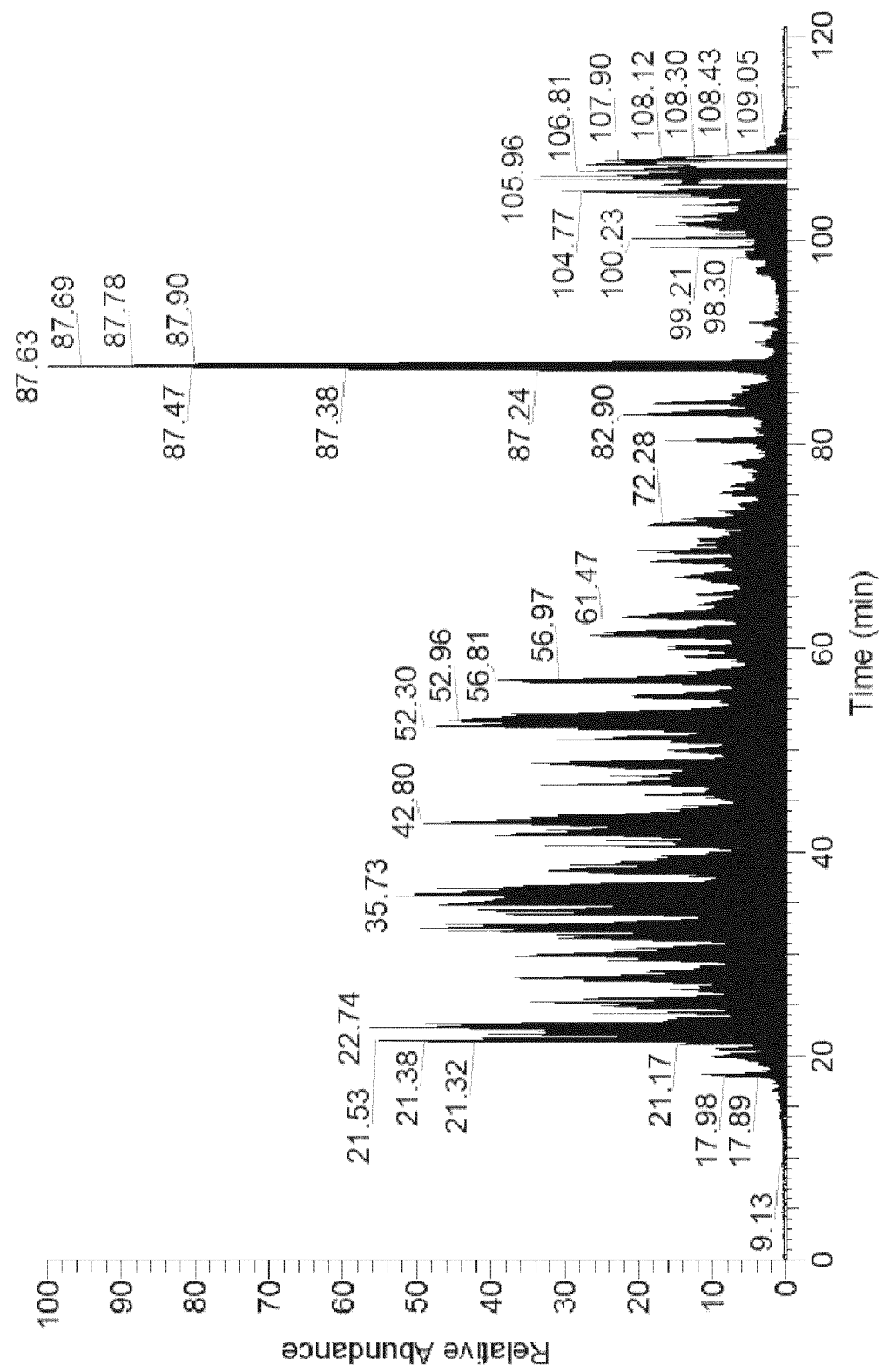
Figure 8D:
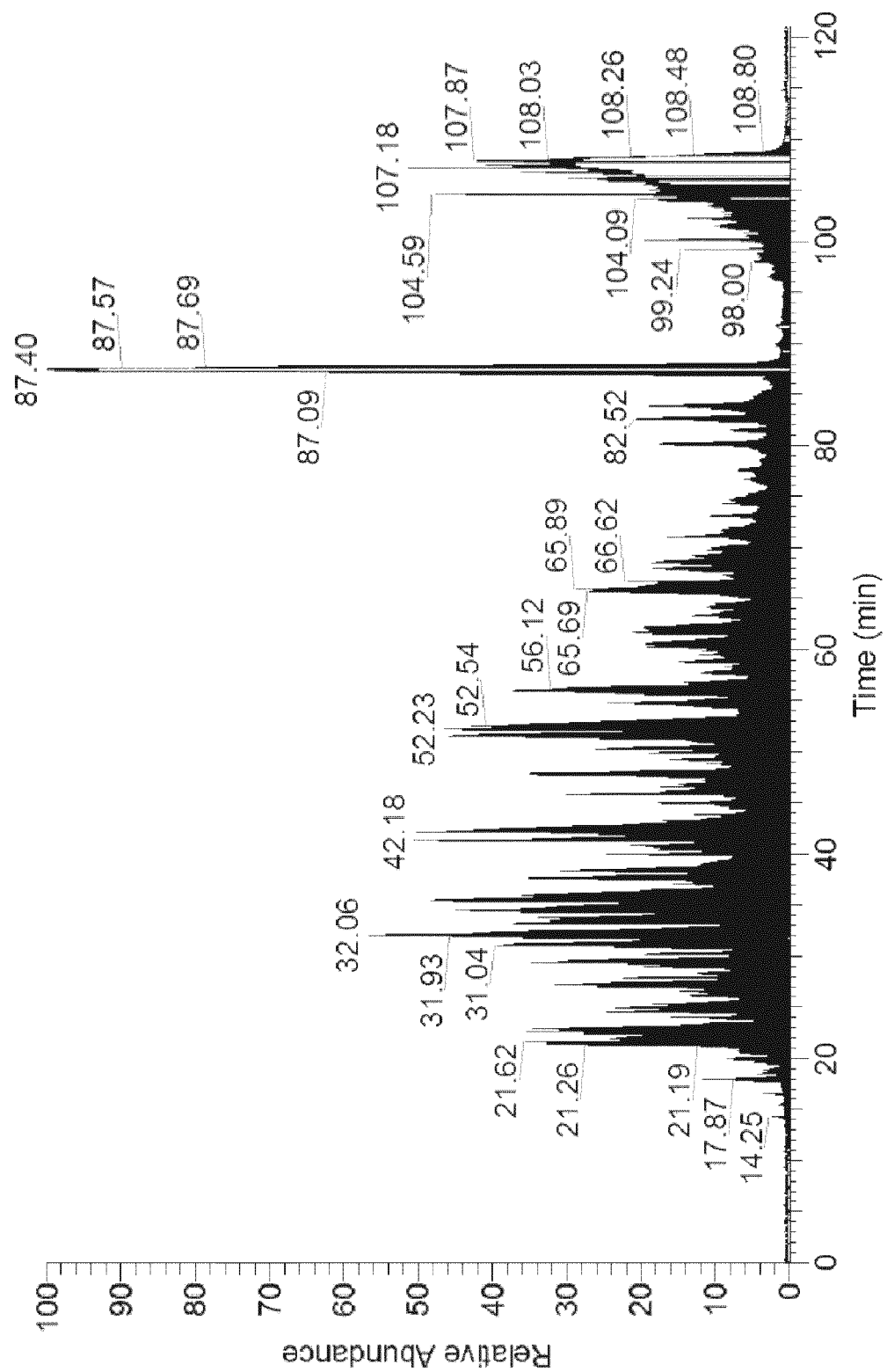
Figure 9A:
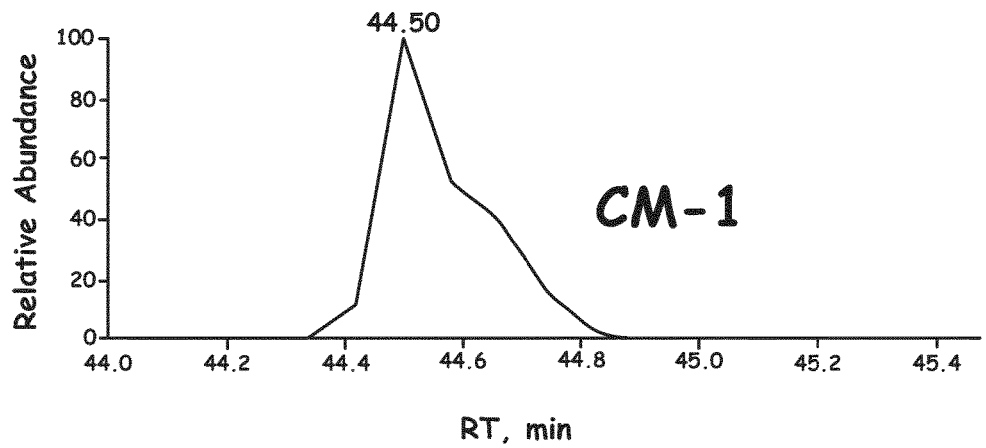
FIG. 9 shows representative extracted ion chromatograms (XICs) (in a zoomed-in region of retention time) for representative signals from a pair of technical replicates (CM-1, CM-2).
Figure 9B:
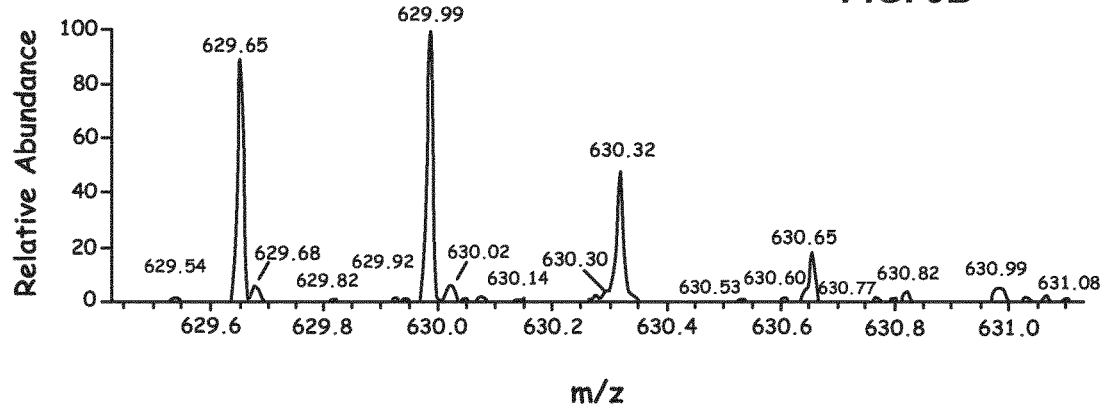
Figure 9C:
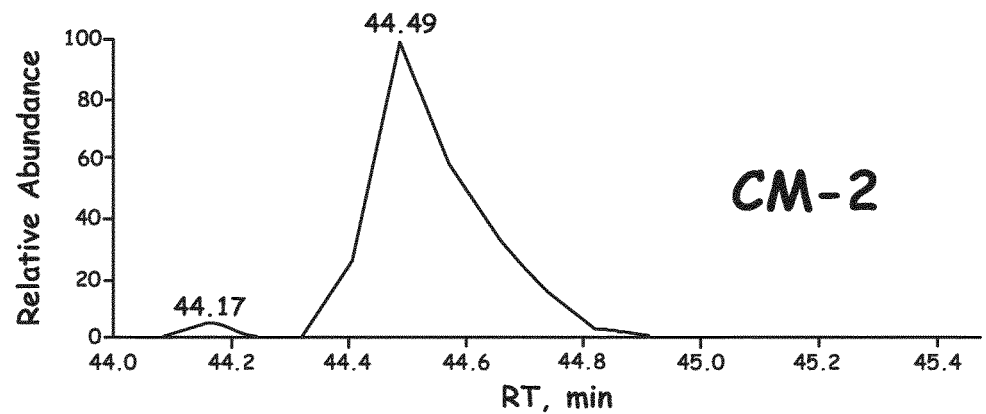
Figure 9D:
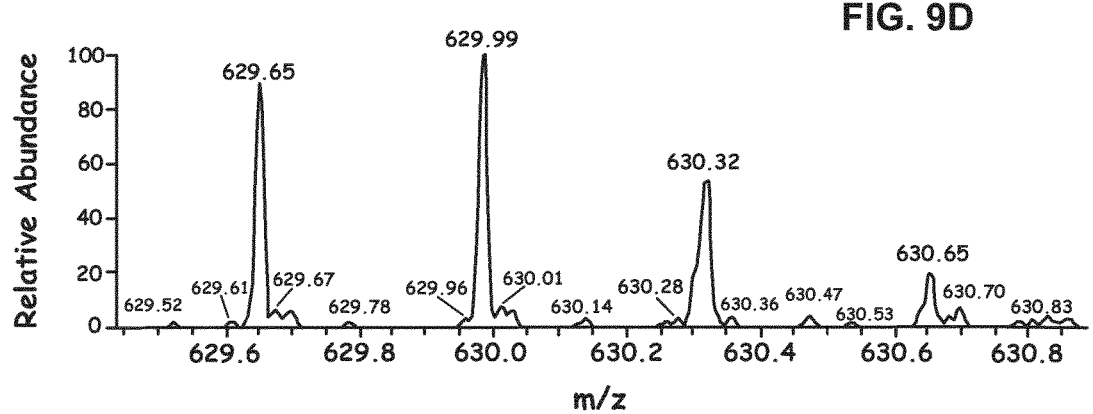
Figure 9E:
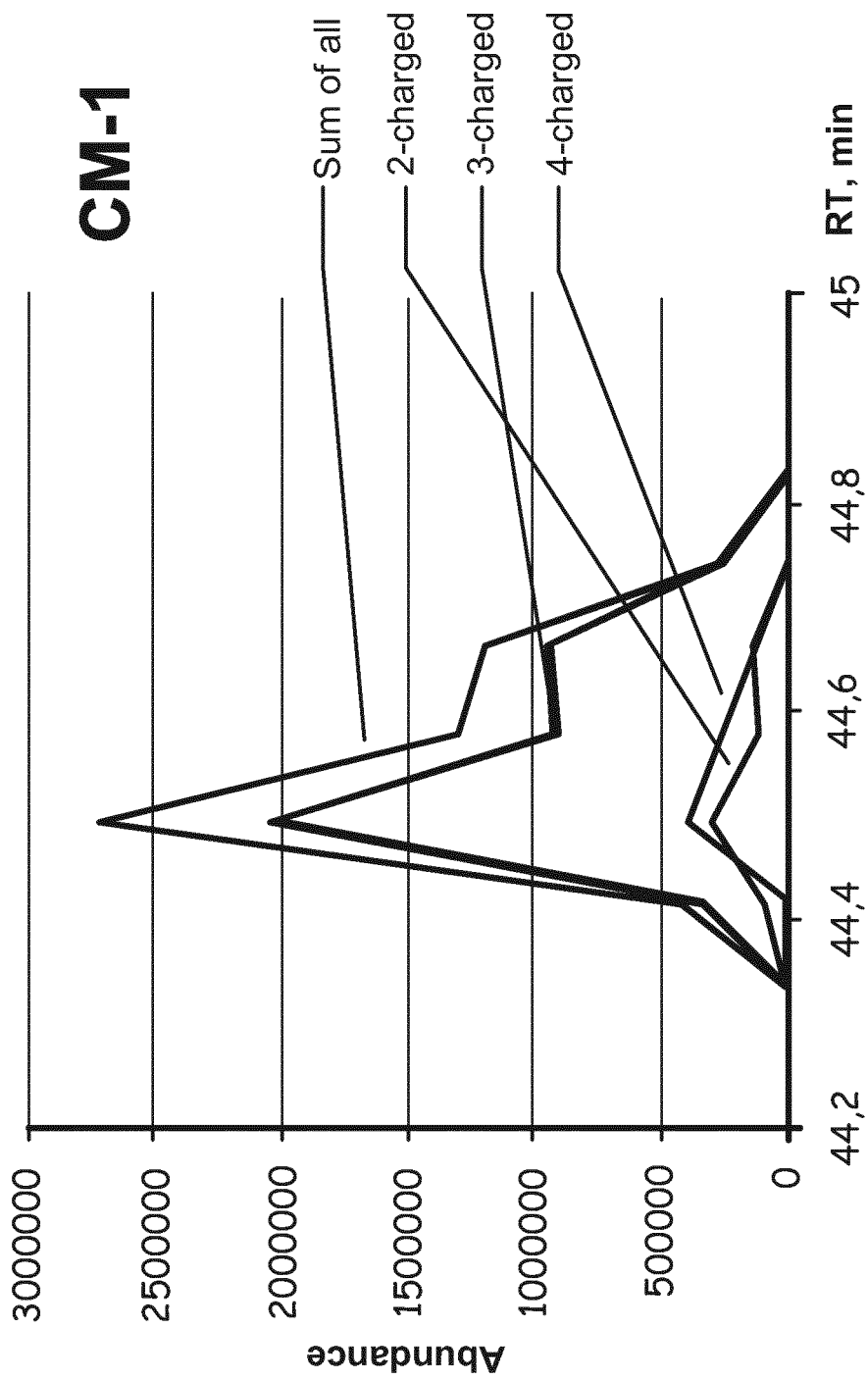
Figure 9F:
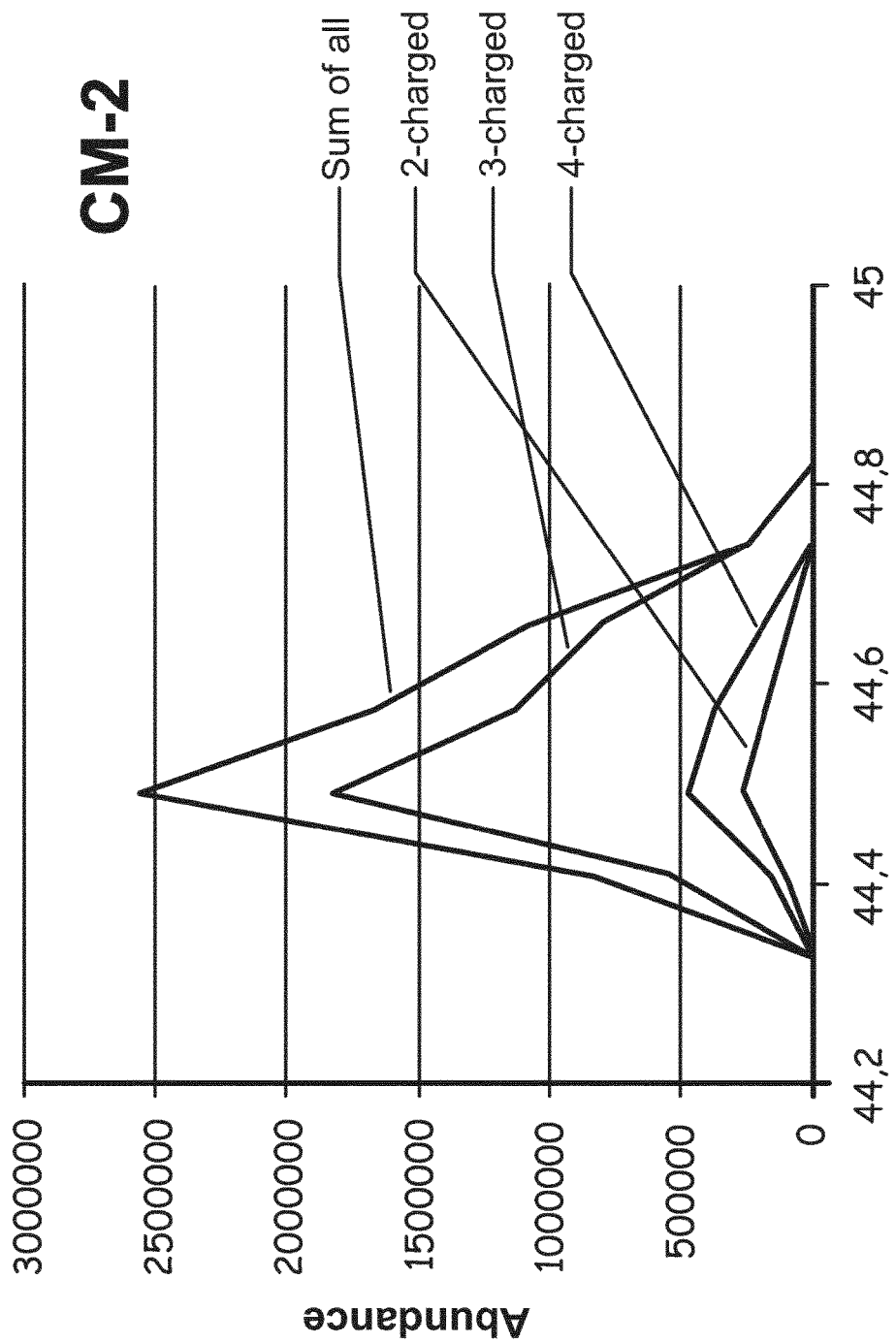

FIG. 6 shows the relative content between male and female blood samples of haptoglobin-related protein (HPR) for data before correction and FIG. 7 shows the data after abundance correction according to the present invention. The y-axis represents peptide abundance in arbitrary units which is plotted for different runs on the x-axis. Referring to FIG. 6, the HPR content is represented by 4 peptides shown by the left hand 4 groups (each of 6 runs) and the right hand 4 groups (each of 6 runs), with the left hand 4 groups being from the male sample and right hand 4 groups being from the female sample, the female with generally lower HPR content. The average coefficient of variation (CV) within the groups is 22% in the data before correction shown in FIG. 6. The corresponding data after correction is shown in FIG. 7 where the improvement in the data quality is clear to see and the average CV within the groups is 7%.

Data Acquisition and Processing

The acquisition of the data and its processing in the example is now described in detail.

The 8 blood samples mentioned above each represented different degrees of Alzheimer disease, for male and female patients separately, as shown in table 3 below:

TABLE 3

|  | Male sample | Female sample |
|---|---|---|
| Healthy | CM | CF |
| Stable memory impairments | M1 | SF |
| Progressive memory impairment | M2 | F2 |
| Well diagnosed Alzheimer disease | M3 | F3 |

For illustration purposes, the total ion current (TIC) of the chromatograms as analysed with Orbitrap MS for two technical replicates of each of CM and M1 groups are shown in FIG. 8. The top left TIC is replicate CM-1, the top right is replicate M1-1, bottom left is replicate CM-2, and the bottom right is replicate M1-2. The suffixes 1 and 2 for each sample CM and M1 designate the two technical replicates in each case, i.e. re-measurements of the same sample. It can be seen from the similarity in the TICs that the majority of peptides are the same in each sample.

(i) Peptide Identification and Retention Time Alignment

Peptides were identified from acquired MS/MS data using a Mascot™ database search. Other programs such as Sequest™ could be used. For this step, all data, i.e. from all 8 samples in the table above, were merged and sent for MS/MS identification using Mascot. This identified about 1200 peptides derived from about 150 proteins. In general, the method thus preferably further comprises a step of identifying the analytes. The identifying of analytes may comprise assigning a composition to each analyte, e.g. an elemental composition, or assigning a peptide, peptide sequence or a peptide/protein ID. The identifying may comprise looking up the analytes by RT (retention time) and/or RO (retention order) and exact mass. The step of identifying analytes is preferably performed prior to determining the apparent analyte abundances.

In the next step, the retention times of the different samples were aligned. It will be appreciated by the skilled person that different methods could be used to align the retention times. In this example the method below was used. In general, the method thus preferably further comprises a step of aligning mass chromatograms constituted by the obtained first set of mass spectral data and the obtained second set of mass spectral data, more preferably before carrying out the process of abundance alignment, e.g. prior to determining the apparent analyte abundances and/or determining a corrected abundance.

The retention time alignment was used to associate signals in the chromatogram with a determined retention time order. It was thus focused on annotating the chromatograms rather than outputting a corrected chromatogram. The alignment was a two stage process conducted as follows.

Retention Time Alignment, Stage 1:
Establishment of the Elution Order.

In a first stage an average elution order is determined. In general, this is done preferably from a plurality of chromatograms assuming a "family" of similar chromatograms (e.g. chromatograms run with the same method on identical samples (technical replicates) or similar chromatograms (e.g. a sample and control; group A vs. related group B; treated vs. untreated samples; etc.) as these are expected to share a majority of signals (typically called the "Matrix" in the case of metabolomics experiments). For such a "family" of similar chromatograms, ideally all chromatograms are used to establish an elution order based on similarities like "identified substances" or "coincidence of elution time, exact mass, and isotopic pattern". In cases of routine analysis the elution order could of course be established on a subset of the total samples, with this elution order e.g. being applied to future measurements of related samples.

The chromatogram data sets for analysis could be simply data as delivered by the instrument, or event lists, as created with a method as described in EP2322922, or simple peak list files extracted from the chromatogram. Examples for the latter are Mascot™ input files (.mgf) or a collection of Sequest™ input files (.dta), which both essentially combine a scan number (or retention time), a parent mass and a list of fragments in a data set, these data sets collectively being a representation of a mass chromatogram. If some form of identification has already been done on the signals (e.g. identification of peptides, or determination of elemental compositions), as in this case, it will help in the process.

Steps of Stage 1:

In the family of chromatography data sets, in each chromatogram "entities" are identified representing a particular substance, e.g. peptide. If a spectrum is to be selected for an entity: the best or maximal example in the chromatogram is taken. Otherwise an "entity" will be identified by one or more exact masses and a chromatographic (i.e. time or scan number) position. In the case of peptides a simple algorithm relies on the MS/MS spectra as submitted to Mascot™ and if a precursor mass was selected more than once multiple MS/MS spectra could belong to the same entity.

For each "entity", entities across the plurality of copies in the family of chromatograms are associated by similarity. In the case of Mascot™ input being used, as in this case, this similarity judgement can be based on a (minimum) number of matching peaks shared between members of the entity family. When "event processing" is used, a family of entities can be established, e.g. by their sharing of accurate mass and isotopic pattern (together with them being within a reasonable retention order window).

From each family of entities the best representative is selected, this can be, for example, the most intense entity.

The entirety of the "best representatives" forms a new chromatographic collection of entities representing in this case peptides, roughly sorted by elution order.

The next step is to determine an average elution order as follows.

For each entity in the collection of best representatives, calculate an "equilibrium value", EV, in the following manner.

For each chromatographic dataset "i":
a) Identify the position where the "current" entity maximises (i.e. identify the best spectrum of the same entity as the current entity of the collection). If this entity is not present in this chromatographic dataset, then the remaining steps of this step are skipped and an EV value is set as EV[i]=0.
b) From this position (spectrum index, which correlates with retention time) count all entities that appear earlier (i.e. at a lower spectrum index or retention time) than the current entity in the current chromatogram, but later (i.e. at a higher spectrum index) than the current entity in the collection. This count is called herein NEV.
c) From the same position count all entities that appear later than the current entity in the current chromatogram, but earlier than the current entity in the collection. This count is called herein PEV.
Therefore, if an entity appears before the current position in both the current chromatogram and the collection it does not affect the count NEV or PEV.
d) Determine EV[i]=NEV−PEV Then, EV=sum of all EV[i].

The result of this is that each entity in the collection is annotated with an EV value for its current position in the collection. The "best" or "average" ordering of the collection (and thus the best or average or "consensus" elution time order) is the ordering that minimizes the sum of all EVs.

One simple way of minimizing the sum of all EVs is the following.

In increasing index position, for each pair of neighbours in the collection it can be tested whether or not the sum of their EVs decreases when they swap position (by determining the EV with the steps a) to d) above for their new position). If the sum of their EVs decreases, then their position should be swapped, otherwise their order should be kept. This process can be repeated until no further swaps are necessary.

The output of stage 1 is a list of entities (which may have identifiers or not) in the order they are expected to elute in a chromatography experiment set up similar to those used as input for Stage 1. This removes the dependency on real retention times, which means a chromatogram need not be "stretched" or "compressed" or "time shifted", because only the enumeration of entities in the most likely order of their appearance one after another is used for comparison.

Retention Time Alignment, Stage 2:

Next a single chromatogram is analyzed at a time, which may or may not be a chromatogram of the input to stage 1.

A "window" is determined for the following steps, consisting of a "time" window and a "mass" window. This may be a user input of a mass and retention time window. The "time" window may be an average chromatographic peak width which is determined from stage 1 or the current data, or may be part of a description of the chromatographic method used, or may be simply a certain number of indices. The "mass" window may be a mass accuracy window obtained from the user, an instrument description or e.g. the variance in the data of stage 1. This "time" or "index" window is herein called RO and the "mass" window is herein called dm.

For each item on the output of stage 1:
i) Find a feature in the chromatogram that matches it within the window defined above. Feature refers to a totality of ion signals for a particular substance. It includes charge and isotope distribution belonging to a particular substance over all retention time. Feature is the sum used for quantification. As in stage 1, only the most intense feature within a chromatogram (i.e. the one closest to the apex of a chromatographic peak) is considered. Less intense ones are simply disregarded.
ii) Calculate a distance value characterizing each feature thus found in the following way:
   a. Identify all entities appearing in the wrong order relative to the current one, i.e. before the current feature in the chromatogram and after it in the stage 1 output, or after the current feature in the chromatogram and before it in the stage 1 output. The process is thus the same as in the determination of NEV and PEV above.
   b. For all these identified entities appearing in the wrong order, determine the distance from the current one.
   c. Calculate the sum of these distances, which is herein called DV. Note: this distance could be expressed in a number of indices as well as in retention time.
iii) Determine the median DV. Consider the features with DV under the median as "found" and the other half as "not found". This means that 50% of the features will be correctly identified in the first run. If a worse rate is expected a lower amount of features should be kept in the first run.

If necessary adjust retention time/index scale to align found features with stage 1 output.

Next the "time" (or index number) window is reduced by a factor of four (i.e. set RO'=RO/4). Then only within this window around the found features (i.e. within about 50% of the total time base) it is searched again for features that match within the reduced "time window", RO', and the full "mass window" dm as defined in the first step. The DVs are determined again but this time only the worst 25% are thrown away (this can be adjusted if more have been thrown away earlier). The entity pairing is then re-run for the remaining features, within RO/2 and with a search window of RO/2. Finally, a run with the full window RO is performed. The purpose of this approach is to obtain first the better matches and only then allow further deviations.

Now all features that are within an acceptable distance from the average retention order are identified. There may be unassigned items on the stage 1 output as well as in the chromatogram used for stage 2 after this.

Extracted Ion Chromatograms (XICs)

After identification of the peptides, extracted ion chromatograms (XICs) were generated wherein all ions from a single peptide were grouped together. FIG. 9 shows representative XICs (in a zoomed-in region of retention time) for representative signals from a pair of technical replicates (CM-1, CM-2). The left panels show the XICs for a single charge state with multiple isotopes, with representative mass spectra also shown below each XIC, and the right panels shows aggregate data for different charge states of the same analyte.

(ii) Local Abundance Correction

A table containing all the identified peptides (i.e. found from all the various runs) was generated. Table 4 below shows part of such a table.

To correct the abundance of each target peptide in turn, the target peptide was first chosen (in Table 4, peptide HRLEDMEQALSPSVFK is highlighted in bold as the target for illustration). Next the neighbouring peptides for that target peptide were chosen. Table 4 shows those peptides that eluted within a time window of approximately 1 minute on either side of the target peptide (approximately 2 minute wide time window). These peptides were considered to be neighbouring peptides.

Figure 10:
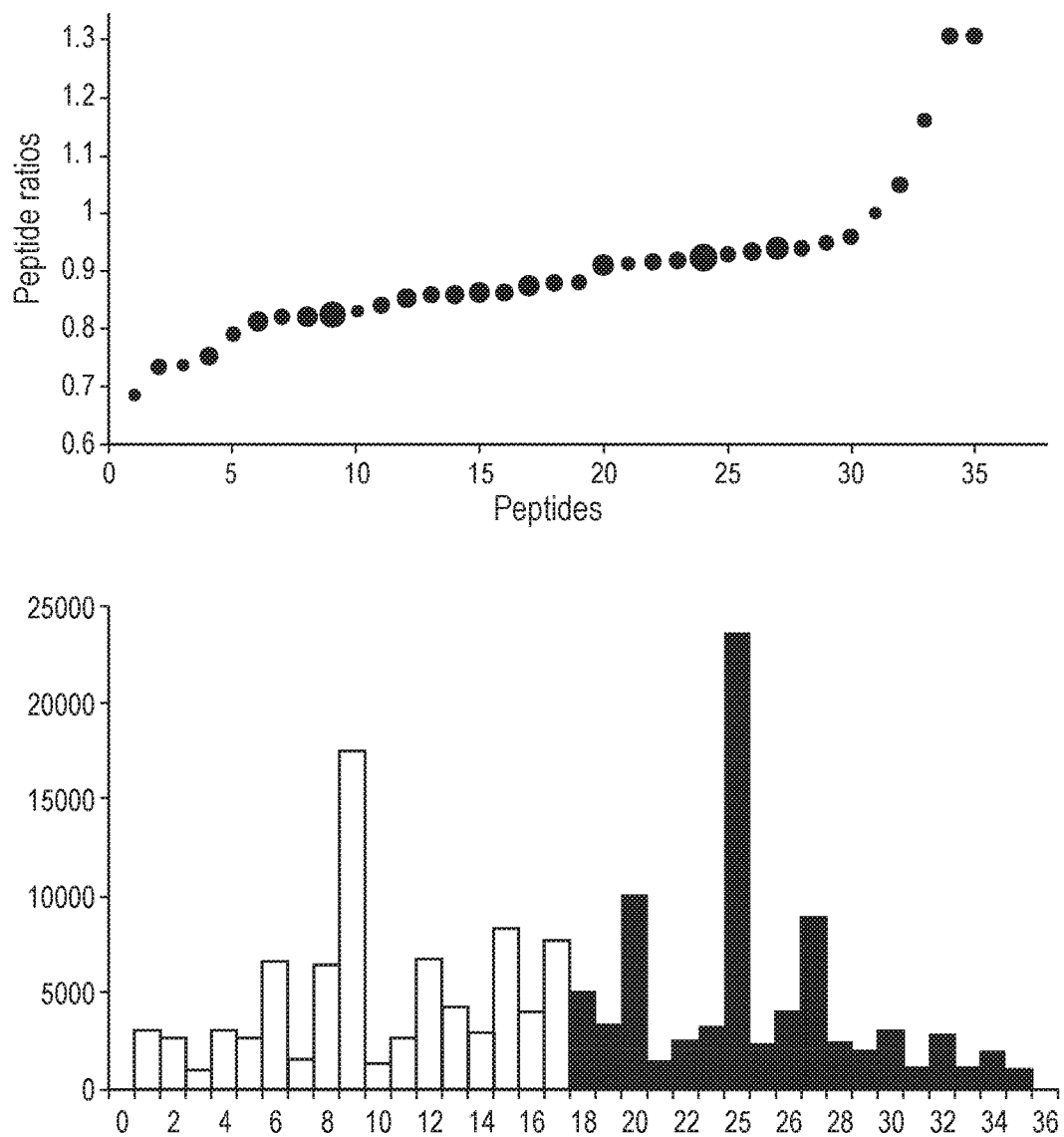
FIG. 10 shows (upper) the ratio of abundances (CM-1/CM-2) for each peptide sorted in increasing order as shown in FIG. 10; and (lower) their associated weights.

From the neighbouring peptides a value was then determined for the abundance correction factor $K_{AV}$ for the target peptide using a general procedure as follows.

a) The ratio, K, of abundances between two samples was determined for each neighbouring peptide, including the target. In Table 4, for illustration, the original (i.e. uncorrected) abundances are given for sample CM-1 (column 4) and sample CM-2 (column 5). The ratio of these abundances (CM-1/CM-2) was calculated for each peptide and is shown in column 6. These original abundance ratios, K, were then sorted in increasing order as shown in FIG. 10 (upper). It can be seen that in this case the ratios range from about 0.68 to 1.31 although the majority of ratios lie between 0.8 and 1.0 with a few outliers at either end. At this point it would have been possible, in an alternative embodiment, to proceed to determine the simple median of the ordered distribution of ratios. However, in this preferred example, the weighted median was determined as follows. The reason for using the "weighted" median is that there is generally more trust to be had in a more intense ion and thus it is desirable to have it contribute more to the median than a less intense ion.

b) Each of the ratios K for the neighbouring peptides was associated with a weight, which is contained in column 7 of Table 4. The weight was calculated as the sqrt(CM-2 abundance), i.e. the square root of the abundance value in column 5. The result of this calculation is also illustrated in FIG. 10 (upper), showing the sorted ratios. The size of the markers for the individual peptide ratios is indicative of the weight associated with it.

c) The list of weights was treated as a step-function w(x), defined between 0.5 and N+0.5 (wherein N is the number of ratios), wherein the weights were ordered in the order of their associated ratios K (see FIG. 10 (lower)).

d) The weighted median m was calculated as the (real, as opposed to integer) index for which the integral of w(x) below m (on the "left" side in the Figure) equals the integral above m (on the "right" side), i.e. $\int_{-\infty}^{m} w(x)dx = \int_{m}^{\infty} w(x)dx$. The resulting weighted median was converted into a ratio $K_{AV}$ ("Correction factor") in column 8 of Table 4, being the K ratio associated with the weighted median. Thus, with the ratios K for all the neighbouring peptides arranged in size order and each K having a weight associated with it, the weighted median of K is given by the K value for which the sum of the weights for the K values below that K value is equal to the sum of the weights for the K values above that K value.

e) The Correction factor $K_{AV}$ was then used to calculate an updated value for one of the intensities (in Table 4, CM-2, see column 9) so that a corrected ratio could be calculated (in Table 4, CM-2, see columns 10 and 11). As can be seen, this changes the ratio CM-1/CM-2 from 0.916 (col. 6) to 1.042. Given that CM-1 and CM-2 are re-measurements of the same sample (thus ideally having a ratio of 1) this can immediately be assessed as a significant improvement.

(iii) Calculating Protein Ratios

In a similar way, the ratios of all identified peptides in all the samples were determined and corrected. These peptide ratios were then used to calculate protein ratios as follows.

By way of example, the protein associated with the peptide analyzed above (HRLEDMEQALSPSVFK) is visualized in Table 5. For comparison with a prior art case, an additional column giving an abundance after being "globally normalized" based on the total ion current integral has been added (column 6), together with the resulting normalised ratios (column 9). For the global normalization all the abundance values of CM-2 were multiplied by the same global normalization factor 0.72477 which made the sum of all the measured abundances for CM-1 equal to the sum of all the measured abundances for CM-2. The resulting globally normalised ratio is clearly a deterioration in the abundance alignment for the peptide analysed above ((HRLEDMEQALSPSVFK) compared to the corrected ratio determined using the method of the present invention (column 10).

Figure 11:
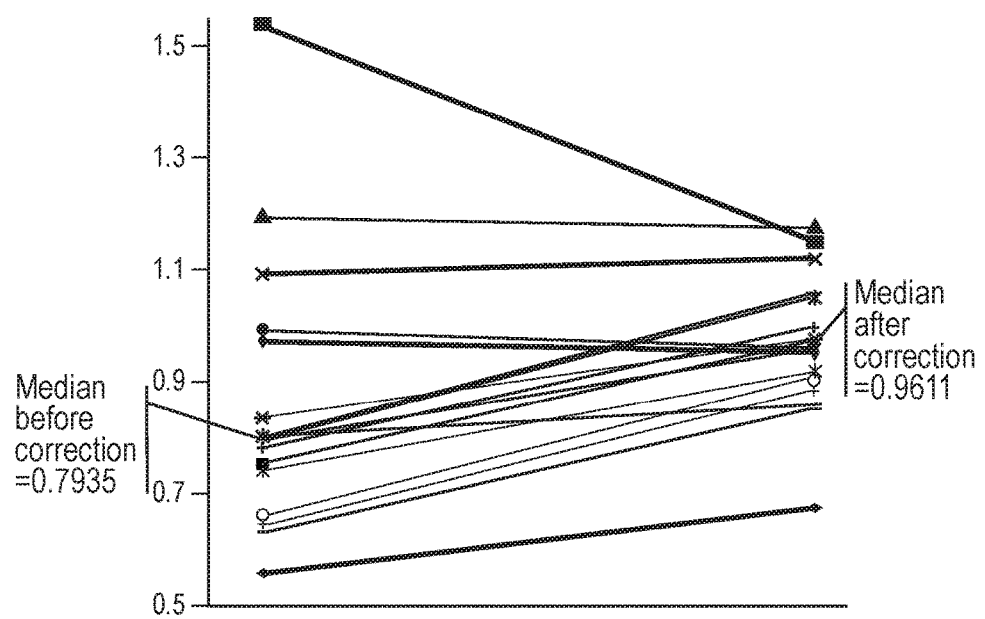
FIG. 11 shows the change of the median of the ratio of abundances (CM-1/CM-2) upon correction.

The abundance ratios of the peptides from the protein were used to calculate a median value (as before a weighted median could be used, e.g. based on some level of confidence for the peptides, but here a conventional median was used). The median changed from 0.7935 based on the data before the correction to 0.9611 based on the data after correction (see Tables 6 and 7 and also FIG. 11). A comparison with the prior art total ion current based renormalization showed the changes for this protein were quite drastic and the corrected median is far closer to the expectation value (1:1 ratio for the identical samples).

Tables 6 and 7 also show the peptide abundance ratios (ordered in size order for determination of medians) for the different possible sample pairings when evaluating 2 Control Group samples (CM-1, CM-2) against 2 Alzheimer samples (M3-1, M3-2). The determined medians for all the sample pairings were then evaluated as follows. The median values were entered into a reference matrix of all the pair-wise ratios (Tables 8 and 9). The expression ratios are then given by the ratios of the geometric means of the columns.

While there does not seem to be a trend in the data before correction (not even between the technical replicates), after correction the ratio between technical replicates is virtually 1 (CM-1/CM-2=0.938/0.925=1.01 and M3-1/M3-2=1.072/ 1.073=1.00) and the ratios between control groups and Alzheimer Disease groups are about 0.87. This may be significant variation in the analyte and thus the analyte may be reported. A marker for the disease may be found from this or other analytes reported using the method of the invention.

Figure 12:
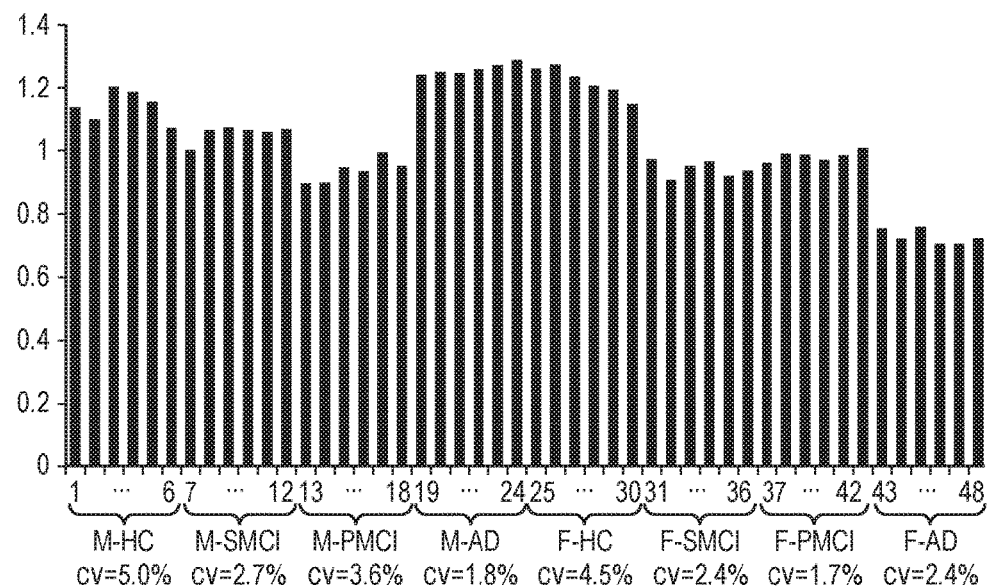
FIG. 12 shows a corrected dataset for a selected protein.
Figure 13:
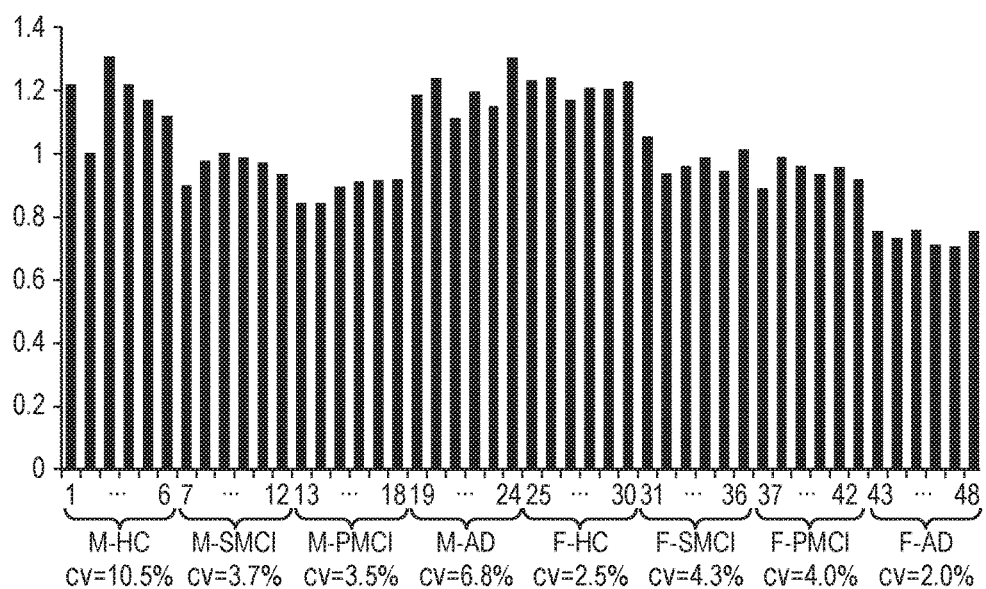
FIG. 13 shows the uncorrected data corresponding to FIG. 12.

FIG. 12 shows the complete corrected dataset for the selected protein. Even though a trend is already visible in the uncorrected data (FIG. 13), for the corrected data it is very clear that this protein has different expression levels in the female population between cases with Alzheimer disease and without. In contrast to that, for the male population the protein has non-differentiating potential between the group with Alzheimer Disease and the control group. Especially for the male control group data the reduction of spread is quite distinct. Key to FIGS. 11 and 12: Male (M); Female (F); Healthy (HC); Stable memory impairments (SMCI); Progressive memory impairment (PMCI); Well diagnosed Alzheimer disease (AD).

TABLE 4

| Peptide | RT: CM-1 | RT: CM-2 | Abundance CM-1 (original) | Abundance CM-2 (original) | Ratio, K [CM-1/CM-2] (original) |
|---|---|---|---|---|---|
| MTSNFPVDLSDYPK, Ox. (M) @#1 | 43.3505 | 43.5017 | 8767151 | 8355186 | 1.04931 |
| TGLLLLSDPDK | 43.6005 | 43.5442 | 1692126 | 1455869 | 1.16228 |
| DQYELLCLDNTR | 43.924 | 43.8379 | 23093164 | 26273742 | 0.87894 |
| TMTIHNGMFFSTYDR | 44.0947 | 44.0032 | 5954331 | 7079641 | 0.84105 |
| YVGGQEHFAHLLILR | 44.008 | 44.0032 | 35491445 | 43847465 | 0.80943 |
| YYCFQGNQFLR | 44.0947 | 44.0884 | 90644988 | 99569751 | 0.91037 |
| SELTQDPAVSVALGQTVR | 43.3505 | 44.0884 | 7378961 | 8587760 | 0.85924 |
| DIVMTQSPDSLAVSLGER, Ox. (M) @#4 | 44.495 | 44.0884 | 5749197 | 6121519 | 0.93918 |

TABLE 4-continued

| Peptide | RT: CM-1 | RT: CM-2 | Abundance CM-1 (original) | Abundance CM-2 (original) | Ratio, K [CM-1/CM-2] (original) |
|---|---|---|---|---|---|
| EIETYHNLLEGGQEDFESSGAGK | 44.1742 | 44.1664 | 1018076 | 1484156 | 0.68596 |
| LVRPEVDVMCTAFHDNEETFLK, Ox. (M) @#9 | 44.254 | 44.1664 | 2.53E+08 | 3.06E+08 | 0.82515 |
| ANTVQEATFQMELPK | 43.924 | 44.1664 | 5254823 | 7161452 | 0.73377 |
| AIQLTYNPDESSKPNMIDAATLK | 44.0947 | 44.3269 | 73942216 | 78823520 | 0.93807 |
| FAFNYLR | 44.3355 | 44.3269 | 10345625 | 11748439 | 0.88060 |
| TPSAAYLWVGTGASEAEK | 44.495 | 44.4084 | 9115794 | 9511180 | 0.95843 |
| GEWTCIAYSQLR | 44.254 | 44.4084 | 669891.7 | 909154.3 | 0.73683 |
| DYVSQFEGSALGK | 44.495 | 44.491 | 5.14E+08 | 5.59E+08 | 0.92085 |
| DLLFRDDTVCLAK | 44.495 | 44.491 | 39064957 | 45872111 | 0.85161 |
| VTTSQDMLSIMEK | 44.495 | 44.491 | 5298477 | 4052093 | 1.30759 |
| HRLEDMEQALSPSVFK | 44.495 | 44.491 | 5874901 | 6411318 | 0.91633 |
| NVVYTCNEGYSLIGNPVAR | 44.5779 | 44.5757 | 2036259 | 2232342 | 0.91216 |
| SSSNEEVMFLTVQVK, Ox. (M) @#8 | 44.6622 | 44.5757 | 1623089 | 1239598 | 1.30937 |
| LQDFSDQLSDYYEK | 44.7434 | 44.6595 | 6909420 | 9204126 | 0.75069 |
| SETEIHQGFQHLGQLFAK | 44.495 | 44.6595 | 5497635 | 6966024 | 0.78921 |
| VFSNGADLSGVTEEAPLKLSK | 44.7434 | 44.7395 | 1412903 | 1702392 | 0.82995 |
| AEDHFSVIDFNQNIR | 44.7434 | 44.7395 | 14040252 | 16273166 | 0.86279 |
| LYGSEAFATDFQDSAAAK | 44.7434 | 44.7395 | 51748521 | 59253609 | 0.87334 |
| WQEGNVFSCSVMHEALHNHYTQK | 44.7434 | 44.7395 | 15653412 | 16789203 | 0.93235 |
| ISETSLPPDMYECLR | 44.827 | 44.8194 | 1382150 | 1383030 | 0.99936 |
| DLLLPQPDLR | 44.9117 | 44.8194 | 5452553 | 5868941 | 0.92905 |
| LSSWVLLMK | 44.9117 | 44.8194 | 60241053 | 69906783 | 0.86173 |
| NLQNNAEWVYQGAIR | 44.9117 | 44.9062 | 15590895 | 18145211 | 0.85923 |
| DKVNSFFSTFK | 44.9919 | 44.987 | 9530087 | 10384509 | 0.91772 |
| WLHPNYSQVDIGLIK | 44.9919 | 44.987 | 34167799 | 41660172 | 0.82016 |
| FVTWIEGVMR | 45.154 | 45.0829 | 1918518 | 2340290 | 0.81978 |
| TYMLAFDVNDEK | 45.2569 | 45.251 | 3930875 | 4142983 | 0.94880 |

| Peptide | Weights v(CM-2) | Correction factor ($K_{AV}$) | Abundance CM-2 (corrected) | Ratio, K corrected [CM-1/CM-2] | Ratios corrected [CM-2/CM-1] |
|---|---|---|---|---|---|
| MTSNFPVDLSDYPK, Ox. (M) @#1 | 2890.534 | 0.8874 | 7414392 | 1.18245 | 0.84570 |
| TGLLLLSDPDK | 1206.594 | 0.8877 | 1292375 | 1.309315 | 0.76376 |
| DQYELLCLDNTR | 5125.792 | 0.8818 | 23168186 | 0.996762 | 1.00325 |
| TMTIHNGMFFSTYDR | 2660.760 | 0.8861 | 6273270 | 0.949159 | 1.05356 |
| YVGGQEHFAHLLILR | 6621.742 | 0.8861 | 38853238 | 0.913475 | 1.09472 |
| YYCFQGNQFLR | 9978.464 | 0.8867 | 88288498 | 1.026691 | 0.97400 |

TABLE 4-continued

| Peptide | RT: CM-1 | RT: CM-2 | Abundance CM-1 (original) | Abundance CM-2 (original) | Ratio, K [CM-1/CM-2] (original) |
|---|---|---|---|---|---|
| SELTQDPAVSVALGQTVR | 2930.488 | 0.8867 | 7614767 | 0.969033 | 1.03196 |
| DIVMTQSPDSLAVSLGER, Ox. (M)@#4 | 2474.170 | 0.8867 | 5427951 | 1.059184 | 0.94412 |
| EIETYHNLLEGGQEDFESSGAGK | 1218.260 | 0.8867 | 1316001 | 0.773613 | 1.29264 |
| LVRPEVDVMCTAFHDNEETFLK, Ox. (M) @#9 | 17501.110 | 0.8867 | 271586229 | 0.931564 | 1.07459 |
| ANTVQEATFQMELPK | 2676.089 | 0.8867 | 6350059 | 0.827523 | 1.20842 |
| AIQLTYNPDESSKPNMIDAATLK | 8878.261 | 0.879 | 69285874 | 1.067205 | 0.93703 |
| FAFNYLR | 3427.600 | 0.879 | 10326878 | 1.001815 | 0.99819 |
| TPSAAYLWVGTGASEAEK | 3084.020 | 0.879 | 8360327 | 1.090363 | 0.91713 |
| GEWTCIAYSQLR | 953.496 | 0.879 | 799147 | 0.838258 | 1.19295 |
| DYVSQFEGSALGK | 23637.310 | 0.879 | 491117040 | 1.046594 | 0.95455 |
| DLLFRDDTVCLAK | 6772.895 | 0.879 | 40321585 | 0.968835 | 1.03217 |
| VTTSQDMLSIMEK | 2012.981 | 0.879 | 3561790 | 1.487588 | 0.67223 |
| HRLEDMEQALSPSVFK | 2532.058 | 0.879 | 5635763 | 1.042432 | 0.95930 |
| NVVYTCNEGYSLIGNPVAR | 1494.102 | 0.895 | 1997946 | 1.019176 | 0.98118 |
| SSSNEEVMFLTVQVK, Ox. (M) @#8 | 1113.372 | 0.895 | 1109440 | 1.46298 | 0.68354 |
| LQDFSDQLSDYYEK | 3033.830 | 0.8795 | 8095029 | 0.853539 | 1.17159 |
| SETEIHQGFQHLGQLFAK | 2639.323 | 0.8795 | 6126618 | 0.897336 | 1.11441 |
| VFSNGADLSGVTEEAPLKLSK | 1304.757 | 0.8797 | 1497594 | 0.943449 | 1.05994 |
| AEDHFSVIDFNQNIR | 4034.001 | 0.8797 | 14315504 | 0.980772 | 1.01960 |
| LYGSEAFATDFQDSAAAK | 7697.637 | 0.8797 | 52125400 | 0.99277 | 1.00728 |
| WQEGNVFSCSVMHEALHNHYTQK | 4097.463 | 0.8797 | 14769462 | 1.05985 | 0.94353 |
| ISETSLPPDMYECLR | 1176.023 | 0.8801 | 1217204 | 1.135512 | 0.88066 |
| DLLLPQPDLR | 2422.590 | 0.8801 | 5165255 | 1.055621 | 0.94731 |
| LSSWVLLMK | 8361.028 | 0.8801 | 61524959 | 0.979132 | 1.02131 |
| NLQNNAEWVYQGAIR | 4259.720 | 0.88 | 15967786 | 0.976397 | 1.02417 |
| DKVNSFFSTFK | 3222.500 | 0.8763 | 9099945 | 1..047269 | 0.95486 |
| WLHPNYSQVDIGLIK | 6454.469 | 0.8763 | 36506809 | 0.935929 | 1.06846 |
| FVTWIEGVMR | 1529.801 | 0..879 | 2057115 | 0.932626 | 1.07224 |
| TYMLAFDVNDEK | 2035.432 | 0.8777 | 3636296 | 1.081011 | 0.92506 |

TABLE 5

| Peptide | RT CM-1 | RT CM-2 | Abundance CM-1, original | Abundance CM-2 original | Abundance CM-2 normalized (Prior art) |
|---|---|---|---|---|---|
| MEPFHFK | 32.9664 | 32.9405 | 3993775 | 5357817 | 3883190 |
| TLYSSSPR | 19.243 | 19.085 | 1276540 | 2708420 | 1962984 |
| LYHAFSAMK | 29.464 | 29.3985 | 5399771 | 8905305 | 6454308 |
| DFTCVHQALK | 28.907 | 28.8552 | 10374893 | 15624306 | 11324042 |
| FQPTLLTLPR | 47.7989 | 47.8249 | 25464521 | 25228819 | 18285114 |
| LLDSLPSDTR | 31.9384 | 31.7875 | 19157524 | 26127497 | 18936449 |
| TNLESILSYPK | 48.3375 | 48.1364 | 15621041 | 16786997 | 12166727 |
| LVLLNAIYLSAK | 56.4885 | 56.5147 | 16021760 | 13911382 | 10082565 |
| KYPVAHFIDQTLK | 40.3992 | 40.2819 | 15286371 | 16887318 | 12239436 |
| VTTSQDMLSIMEK | 44.495 | 44.491 | 5298477 | 4051939 | 2936727 |
| LEDMEQALSPSVFK | 49.034 | 49.0427 | 5128181 | 5316396 | 3851369 |
| HRLEDMEQALSPSVFK | 44.495 | 44.491 | 5874901 | 6411318 | 4646736 |
| GVTSVSQIFHSPDLAIR | 49.5345 | 49.6145 | 27753705 | 30767622 | 22299477 |
| TLLVFEVQQPFLFVLWDQQHK | 77.213 | 77.211 | 3568168 | 4097073 | 2969439 |
| VETNMAFSPFSIASLLTQVLLGAGENTK | 97.6055 | 97.6479 | 1073682 | 976656.3 | 707852 |
| VETNMAFSPFSIASLLTQVLLGAGENTK + Oxidized M on 5th position | 96.3482 | 96.4754 | 3163916 | 2798120 | 2027996 |
| KVETNMAFSPFSIASLLTQVLLGAGENTK + Oxidized M on 6th position | 91.9047 | 91.8605 | 720229.5 | 788578.3 | 571538.6 |

| Peptide | Abundance CM-2 corrected | Correction Factor | Ratio, [CM-2/CM-1], normalized (Prior art) | Ratio, [CM-2/CM-1], corrected |
|---|---|---|---|---|
| MEPFHFK | 3801486 | 0.7095 | 0.97231 | 0.951853 |
| TLYSSSPR | 1468154 | 0.5421 | 1.537738 | 1.150104 |
| LYHAFSAMK | 6343735 | 0.7124 | 1.195293 | 1.174816 |
| DFTCVHQALK | 11646710 | 0.7454 | 1.091485 | 1.122586 |
| FQPTLLTLPR | 22567966 | 0.8945 | 0.744371 | 0.918722 |
| LLDSLPSDTR | 18412165 | 0.7047 | 0.98846 | 0.961093 |
| TNLESILSYPK | 15571138 | 0.9276 | 0.778868 | 0.996805 |
| LVLLNAIYLSAK | 13650132 | 0.9812 | 0.629304 | 0.851975 |
| KYPVAHFIDQTLK | 13108673 | 0.7762 | 0.800676 | 0.85754 |
| VTTSQDMLSIMEK | 3561790 | 0.879 | 0.554259 | 0.672229 |
| LEDMEQALSPSVFK | 5000044 | 0.9405 | 0.751372 | 0.975013 |
| HRLEDMEQALSPSVFK | 5635763 | 0.879 | 0.790947 | 0.959295 |
| GVTSVSQIFHSPDLAIR | 29219883 | 0.9497 | 0.803477 | 1.052828 |
| TLLVFEVQQPFLFVLWDQQHK | 3482497 | 0.85 | 0.832203 | 0.97599 |

TABLE 5-continued

| Peptide | RT CM-1 | RT CM-2 | Abundance CM-1, original | Abundance CM-2 original | Abundance CM-2 normalized (Prior art) |
|---|---|---|---|---|---|
| VETNMAFSPFSIASLLTQVLLGAGENTK | 974750.5 | 0.998 | | 0.659275 | 0.907858 |
| VETNMAFSPFSIASLLTQVLLGAGENTK + Oxidized M on 5th position | 2804882 | 1.0024 | | 0.640977 | 0.886522 |
| KVETNMAFSPFSIASLLTQVLLGAGENTK + Oxidized M on 6th position | 765114.1 | 0.9702 | | 0.7935551 | 1.06232 |

TABLE 6

(Data before correction)
Peptide Abundance ratios from protein

| CM-2/CM-1 | M3-1/CM-1 | M312/CM-1 | M3-1/CM-2 | M3-2/CM-2 | M3-2/M3-1 |
|---|---|---|---|---|---|
| 0.554259 | Filtered | 0.373796 | Filtered | Filtered | 0.941669 |
| 0.629304 | 0.359827 | 0.452207 | 0.531645 | 0.66115 | 0.953553 |
| 0.640977 | 0.580971 | 0.602366 | 0.715487 | 0.746607 | 0.974456 |
| 0.659275 | 0.695236 | 0.846795 | 0.815726 | 0.837702 | 0.995816 |
| 0.744371 | 0.852133 | 0.859821 | 0.926316 | 1.064917 | 0.996049 |
| 0.751372 | 0.871403 | 0.889419 | 1.056536 | 1.16046 | 1.011979 |
| 0.778868 | 0.924634 | 1.021374 | 1.065421 | 1.295135 | 1.012802 |
| 0.790947 | 1.000977 | 1.062847 | 1.129688 | 1.296808 | 1.017019 |
| Median 0.793551 | 1.048123 | (1.062847 + 1.090617)/2 = 1.076732 | 1.237377 | 1.335347 | 1.023367 |
| 0.800676 | 1.082328 | 1.090617 | 1.27067 | 1.339449 | 1.023665 |
| 0.803477 | 1.109482 | 1.114264 | 1.318989 | 1.4025 | 1.032523 |
| 0.832203 | 1.161568 | 1.120402 | 1.353597 | 1.409686 | 1.039864 |
| 0.97231 | 1.193837 | 1.185646 | 1.410684 | 1.438555 | 1.167201 |
| 0.98846 | 1.205216 | 1.196666 | 1.413129 | 1.449311 | 1.221566 |
| 1.091485 | 1.255645 | 1.223616 | 1.451861 | 1.475581 | 1.260414 |
| 1.195293 | 1.286977 | 1.426766 | 1.579757 | 1.511642 | 1.523435 |
| 1.537738 | Filtered | 1.461309 | Filtered | Filtered | 1.547583 |

TABLE 7

(Data after correction)
Peptide Abundance ratios from protein

| CM-2/CM-1 | M3-1/CM-1 | M312/CM-1 | M3-1/CM-2 | M3-2/CM-2 | M3-2/M3-1 |
|---|---|---|---|---|---|
| 0.672229 | Filtered | 0.438198 | Filtered | Filtered | 0.904951 |
| 0.851975 | 0.605426 | 0.608306 | 0.648865 | 0.636278 | 0.960097 |
| 0.85754 | 0.625204 | 0.70615 | 0.681392 | 0.718519 | 0.980606 |
| 0.886522 | 0.850967 | 0.977238 | 0.83372 | 0.846925 | 0.981649 |
| 0.907858 | 0.978299 | 1.03487 | 0.912159 | 1.027911 | 0.981736 |
| 0.918722 | 0.978712 | 1.042541 | 1.018014 | 1.051442 | 0.98348 |
| 0.951853 | 0.990521 | 1.10661 | 1.086437 | 1.061415 | 0.987004 |
| 0.959295 | 1.121415 | 1.151775 | 1.095078 | 1.114875 | 0.994342 |
| Median 0.961093 | 1.163783 | (1.151775 + 1.154727)/2 = 1.153251 | 1.165087 | 1.126664 | 1.0222 |
| 0.975013 | 1.190085 | 1.154727 | 1.215501 | 1.217304 | 1.029564 |
| 0.97599 | 1.209333 | 1.16178 | 1.27607 | 1.223289 | 1.035489 |
| 0.996805 | 1.214138 | 1.174725 | 1.308323 | 1.303424 | 1.04959 |
| 1.052828 | 1.222217 | 1.178945 | 1.431541 | 1.315174 | 1.058925 |
| 1.06232 | 1.22362 | 1.248335 | 1.443413 | 1.378716 | 1.076316 |
| 1.122586 | 1.511291 | 1.251958 | 1.50686 | 1.43827 | 1.101993 |
| 1.150104 | 2.333249 | 1.35473 | 2.170783 | 1.965635 | 1.407842 |
| 1.174816 | Filtered | 2.025608 | Filtered | Filtered | 1.614455 |

TABLE 8

Protein abundance reference matrix - before correction

| | CM-1 | CM-2 | M3-1 | M3-2 |
|---|---|---|---|---|
| CM-1 | 1 | 0.793551 | 1.048123 | 1.076732 |
| CM-2 | 1.260158 | 1 | 1.237377 | 1.335347 |
| M3-1 | 0.954086 | 0.808161 | 1 | 1.023367 |
| M3-2 | 0.928736 | 0.748869 | 0.977167 | 1 |
| Column Geometric Mean | 1.02796 | 0.832472 | 1.061013 | 1.10137 |

TABLE 9

Protein abundance reference matrix - after correction

| | CM-1 | CM-2 | M3-1 | M3-2 |
|---|---|---|---|---|
| CM-1 | 1 | 0.961093 | 1.163783 | 1.153251 |
| CM-2 | 1.040482 | 1 | 1.165087 | 1.126664 |
| M3-1 | 0.859267 | 0.858305 | 1 | 1.0222 |
| M3-2 | 0.867114 | 0.887576 | 0.978282 | 1 |
| Column Geometric Mean | 0.938339 | 0.925024 | 1.073183 | 1.073528 |

As used herein, including in the claims, unless the context indicates otherwise, singular forms of the terms herein are to be construed as including the plural form and vice versa.

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention claimed is:

1. A computer implemented method of quantifying one or more analytes from mass spectral data, comprising:
    obtaining a first set of mass spectral data from a first set of analytes eluted from a chromatography column;
    obtaining a second set of mass spectral data from a second set of analytes eluted from a chromatography column; wherein a majority of the analytes in each data set are common to both data sets;
    determining apparent abundances of at least some analytes in each data set;
    selecting an analyte as a target analyte and determining for that analyte a plurality of localized neighboring analytes that are close neighbors to the target analyte with respect to retention time, wherein the number of localized neighboring analytes is less than the total number of analytes in each data sets and the number of neighboring analytes is similar or equal either side of the target analyte in retention time;
    determining a locally corrected abundance of the target analyte based on differences between the first and second data sets in the apparent abundance of the determined localized neighboring analytes, by applying a correction factor or factors to an abundance of the target analyte, wherein the correction factor or factors is such that applying the correction factor or factors to the abundances of the neighboring analytes improves the correlation between the apparent abundances of neighboring analytes in the first and second data sets; and
    obtaining an improved quantitation of the target analyte based on its corrected abundance.

2. A method as claimed in claim 1 further comprising selecting one or more further analytes as target analytes and for each such further analyte as a target analyte:
    determining for that further analyte a plurality of localized neighboring analytes by their locality to that further analyte with respect to retention time;
    determining a locally corrected abundance of that further analyte based on differences between the first and second data sets in the apparent abundance of the determined localized neighboring analytes; and
    quantifying that further analyte based on its corrected abundance; wherein the plurality of determined localized neighboring analytes is different for at least some different target analytes.

3. A method as claimed in claim 1 wherein at least 80% of the analytes in each data set are common to both data sets.

4. A method as claimed in claim 1 comprising determining the plurality of localized neighboring analytes as being the analytes that have a retention time within a given time interval spanning the retention time of the target analyte.

5. A method as claimed in claim 4 wherein the width of the time interval is substantially the same as the chromatographic peak width of the target analyte.

6. A method as claimed in claim 4 wherein the width of the time interval is up to 2 minutes.

7. A method as claimed in claim 1 wherein the number n of the determined localized neighboring analytes is from 5 to 100.

8. A method as claimed in claim 1 wherein the majority of the localized neighboring analytes are substantially unchanged in actual abundance between the first and second data sets.

9. A method as claimed in claim 1 wherein determining the locally corrected abundance of the target analyte comprises: determining a correction factor or factors based on said differences between the first and second data sets in abundance of the determined localized neighboring analytes and applying the correction factor or factors to the abundance of the target analyte to determine the corrected abundance.

10. A method as claimed in claim 9 wherein determining the correction factor or factors comprises: determining a value $K_{AV}$ representing a central tendency value from the determined localized neighboring analytes of a ratio, K, wherein K is for each neighboring analyte a ratio of its abundance in the first set of mass spectral data and its abundance in the second set of mass spectral data.

11. A method as claimed in claim 10 wherein outlying K values are excluded from determining the value, $K_{AV}$.

12. A method as claimed in claim 11 wherein a median K value is selected as $K_{AV}$.

13. A method as claimed in claim 12 wherein the median K value is a weighted median.

14. A method as claimed in claim 10 wherein the ratio K is a weighted ratio of the abundances in the first set of mass spectral data and second set of mass spectral data.

15. A method as claimed in claim 1 further comprising aligning mass chromatograms constituted by the obtained first set of mass spectral data and the obtained second set of mass spectral data.

16. A method as claimed in claim 10 wherein the method comprises determining a corrected abundance ratio, $K_{cor}$, according to $K_{cor}=K_{targ}/K_{AV}$, where $K_{targ}$ is the ratio of the abundance of the target analyte in the first set of mass spectral data and its abundance in the second set of mass spectral data.

17. A method as claimed in claim 1 comprising creating an extracted ion chromatogram (XIC) of the analytes for each data set and from the XIC determining the apparent analyte abundances.

18. A method as claimed in claim 1 further comprising identifying the analytes prior to determining the apparent analyte abundances.

19. A method as claimed in claim 1 whereby the effect of electrospray current fluctuation between obtaining different data sets is reduced.

20. A method as claimed in claim 1 wherein the analytes are selected from the group consisting of proteins, peptides, lipids, pharmaceuticals and/or metabolites.

21. Use of a method as claimed in claim 1 for finding a marker for a disease.

22. A non-transitory computer readable medium carrying a computer program having elements of program code for carrying out the method of claim 1.

* * * * *